(12) United States Patent
Bachalo et al.

(10) Patent No.: US 7,788,067 B2
(45) Date of Patent: Aug. 31, 2010

(54) MEANS AND METHODS FOR SIGNAL VALIDATION FOR SIZING SPHERICAL OBJECTS

(75) Inventors: William D. Bachalo, Los Altos Hills, CA (US); Gregory Allan Payne, Richland, WA (US)

(73) Assignee: Artium Technologies, Inc., Sunnyvale, CA (US)

( * ) Notice: Subject to any disclaimer, the term of this patent is extended or adjusted under 35 U.S.C. 154(b) by 202 days.

(21) Appl. No.: 11/433,005

(22) Filed: May 12, 2006

(65) Prior Publication Data

US 2007/0263215 A1 Nov. 15, 2007

(51) Int. Cl.
*H03F 13/00* (2006.01)

(52) U.S. Cl. .................. 702/193; 702/189; 702/191; 702/194

(58) Field of Classification Search .............. 702/57, 702/58, 66, 75, 79, 182, 189; 250/574; 356/345, 356/484, 125; 385/125; 436/518; 700/5
See application file for complete search history.

(56) References Cited

U.S. PATENT DOCUMENTS

| | | |
|---|---|---|
| 3,966,324 A | 6/1976 | Iten |
| 4,329,054 A | 5/1982 | Bachalo |
| 4,540,283 A | 9/1985 | Bachalo |
| 4,697,922 A | 10/1987 | Gunter et al. |
| 4,700,129 A | 10/1987 | Yoshizawa |
| 4,701,051 A | 10/1987 | Buchhave et al. |
| 4,807,990 A | 2/1989 | Keefer |
| 4,838,687 A | 6/1989 | Pfeifer |
| 4,843,894 A * | 7/1989 | Yashiro et al. .............. 73/865.5 |

(Continued)

FOREIGN PATENT DOCUMENTS

DE 199 54 702 A1 5/2001

(Continued)

OTHER PUBLICATIONS

S.V. Sankar, et al., "Performance Analysis of Various Phase Doppler Systems", presented at 4th International Congress on Optical Particle Sizing, Nuremberg, Germany (Mar. 21-23, 1995), pp. 1-21.

(Continued)

*Primary Examiner*—Hal D Wachsman
*Assistant Examiner*—Felix E Suarez
(74) *Attorney, Agent, or Firm*—Blakely, Sokoloff, Taylor & Zafman LLP

(57) ABSTRACT

Methods and apparatuses for validating signals to determine sizes and velocities of spherical objects are described. Light is scattered from a spherical object to form an interference fringe pattern. Portions of the interference fringe pattern are received by photodetectors. In response, the photodetectors generate time varying electrical signals. At least one of the time varying signals is partitioned into timing segments. The timing segments are processed to determine one or more timing parameters. A timing parameter consistency between at least two of the timing segments is verified. At least one of the time varying signals is validated based on the timing parameter consistency. The time varying electrical signal is accepted if a timing parameter difference is less or equal to a predetermined timing parameter error threshold. The time varying electrical signal is rejected if the timing parameter difference is larger than the predetermined timing parameter error threshold.

42 Claims, 17 Drawing Sheets

U.S. PATENT DOCUMENTS

| | | | |
|---|---|---|---|
| 4,854,705 | A | 8/1989 | Bachalo |
| 4,986,659 | A | 1/1991 | Bachalo |
| 5,289,391 | A | 2/1994 | Ibrahim et al. |
| 5,296,910 | A | 3/1994 | Cole |
| 5,684,587 | A | 11/1997 | Naqwi |
| 5,784,160 | A * | 7/1998 | Naqwi ........................ 356/496 |
| 5,808,895 | A | 9/1998 | Ibrahim et al. |
| 6,587,208 | B2 * | 7/2003 | Maeda et al. ............... 356/496 |
| 6,654,102 | B1 | 11/2003 | Modares et al. |
| 6,999,171 | B2 * | 2/2006 | Kusuzawa ................... 356/336 |
| 7,126,694 | B1 * | 10/2006 | Bachalo ...................... 356/484 |
| 2007/0263215 | A1 | 11/2007 | Bachalo et al. |

FOREIGN PATENT DOCUMENTS

| | | |
|---|---|---|
| EP | 1 855 081 A1 | 11/2007 |
| WO | WO 01/36937 | 5/2001 |

OTHER PUBLICATIONS

Peter A. Strakey, et al., "Phase-Doppler Interferometry with Probe-to-Droplet Size Rations Less Than Unity. I. Trajectory Errors", Applied Optics, vol. 39, No. 22, pp. 3875-3886 (Aug. 1, 2000).

Peter A. Strakey, et al., "Phase-Doppler Interferometry with Probe-to-Droplet Size Ratios Less than Unity. II. Application of the Technique", Applied Optics, vol. 39, No. 22, pp. 3887-3893 (Aug. 1, 2000).

W.D. Bachalo, et al., "Development of the Phase/Doppler Spray Analyzer for Liquid Drop Size and Velocity Characterizations", AIAA/SAE/ASME 20th Joint Propulsion Conference, Cincinnati, Ohio, American Institute of Aeronautics and Astronautics, New York, Jun. 11-13, 1984, pp. 1-13.

W.D. Bachalo, et al., "Phase/Doppler Spray Analyzer for Simultaneous Measurements of Drop Size and Velocity Distributions", Optical Engineering, vol. 23, No. 5, pp. 583-590 (Sep./Oct. 1984).

W.D. Bachalo, et al., "Method for Measuring the Size and Velocity of Spheres by Dual-Beam Light-Scatter Interferometry", Applied Optics, vol. 19. No. 3, pp. 363-370 (Feb. 1, 1980).

W.D. Bachalo, et al., "5.0 Phase Doppler Particle Analyzer (PDPA)", a chapter from "A Handbook of Fluid Dynamics" by R. W. Jhnson, CRC Press (Washington, D.C. 1998).

"CrystaLaser" product information document, 7pp.

D.L. Black, et al., "Laser-based techniques for particle-size measurement: a review of sizing methods and their industrial applications," XP004068954, Progress in Energy and Combusting Science, vol. 22, No. 3, pp. 267-306 (1996).

European Search Report for EPO Application No. EP 07 25 1979, 2 pgs. (Aug. 1, 2007).

European Search Report for EPO Application No. EP 07 25 2775.7, 4 pgs. (Sep. 27, 2007).

Kapulla, Ralf, et al., "Operation conditions of a phase Doppler anemometer: droplet size measurements with laser beam power, photomultiplier voltage, signal gain and signal-to-noise ratio as parameters," XP020103365, Measurement Science and Technology, Institute of Physics Publishing, Bristol, Great Britain, vol. 17, No. 1, pp. 221-227 (Jan. 1, 2006).

Saffman, M. "Automatic calibration of LDA 1-22 measurement volume size," XP002452852, Applied Optics, vol. 26, No. 13, pp. 2592-2597 (Jul. 1, 1987).

Lexis Summary of European Patent Application No. 1238258, 3 pages (Sep. 11, 2002).

Qiu et al., "A Reliable Method for Determining the Measurement Volume Size and Particle Mass Fluxes Using Phase-Doppler Anemometry", Experiments in Fluids, 13, pp. 393-404, Springer-Verlag, 1992.

Bachlo et al., "Analysis And Testing of a New Method for Drop Size Measurement Using Laser Light Scatter Interferometry", Phase Doppler Interferometry (PDI), NASA Contractor Report No. 174636, Aerometrics, Inc. Mountain View CA, 1984, 12 pages.

* cited by examiner

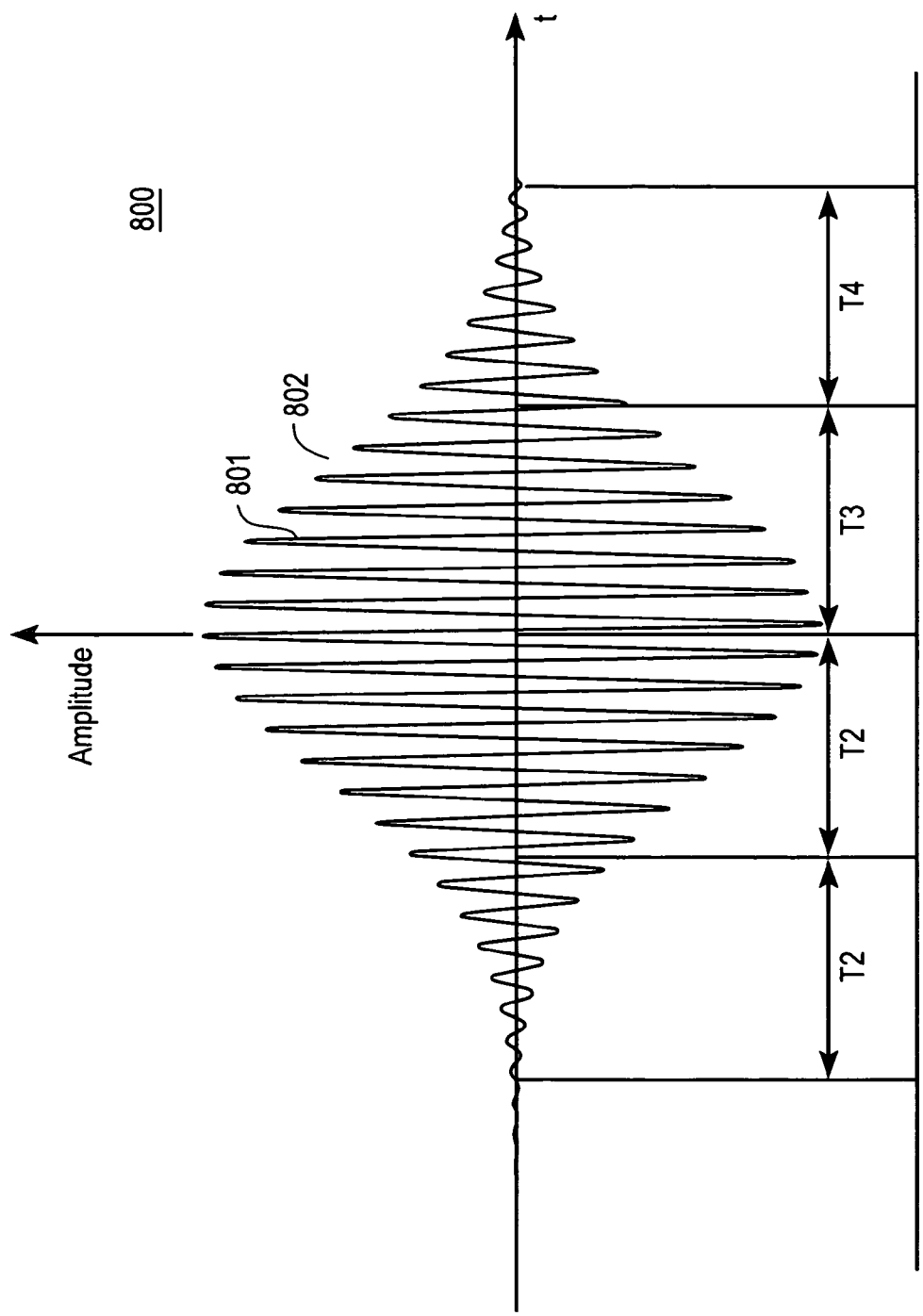

MEANS AND METHODS FOR SIGNAL VALIDATION FOR SIZING SPHERICAL OBJECTS

FIELD

Embodiments of the invention relate to devices to characterize spherical objects, including particles, droplets, bubbles, and the like. More particularly, embodiments of the invention relate to devices that characterize spherical objects, including particles, droplets, bubbles, and the like, using light scattering interferometry.

BACKGROUND

Information on size and velocity of spherical objects including particles, droplets, bubbles, etc., is important for numerous applications in various industries. These applications include, for example, fuel spray combustion analysis and control for the automotive industry, aircraft gas turbine combustion, inhaler manufacturing for the pharmaceutical industry, household spray systems manufacturing, agricultural pesticide application, aircraft icing analysis and control, spray nozzle manufacturing, atmospheric aerosol analysis, atmospheric studies, and various combustion related applications.

Normally, a laser light scattering interferometry technique is used to determine the size and velocity of spherical objects, such as particles, drops, bubbles, etc. According to this technique, spherical objects pass the intersection point of two crossed laser beams generated from the same laser. The two crossed laser beams form a sample volume at the intersection point. The light scattered by the spherical object, as it passes through the sample volume, produces an interference fringe pattern at the plane of the detector. The spatial period of the interference fringe pattern produced by the light scattered from the spherical object, as it passes through the sample volume, may be used to determine the size of the spherical object and a velocity component of the spherical object.

The light produced by each of the two crossing laser beams is scattered from the spherical object due to various mechanisms, e.g., reflection and refraction. The light scattered from the spherical object by different mechanisms that cannot be reliably separated is mixed to form the interference fringe pattern that is a complex superposition of several interference patterns having several spatial frequency components. Furthermore, if more than one particle passes or resides in the sample volume at one time, there may be a change in the signal frequency and phase of the signals leading to an error in the measurement.

Such complex interference fringe patterns deviate significantly from a sinusoidal fringe pattern formed by the light scattered from single spherical object due to a single light scattering mechanism. The complex interference fringe pattern formed by interference between the different light scattering mechanisms, e.g., refraction and reflection, varies in time and space as the spherical object moves through the sample volume. The complex non-periodic interference pattern with varying spatial period leads to significant errors in determining the size and velocity of the spherical object. The problem is intensified in high particle density environments, when highly focused laser beams having Gaussian beam intensity distributions are used.

FIG. 1 illustrates drops having different relative diameters to the focused Gaussian beam diameter that pass Gaussian laser beams 110-130. As shown in FIG. 1, each of the laser beam intensity profiles 112, 122, and 132 has a waist diameter Dw. A particle 111 has the diameter d smaller than diameter Dw, such that $\Gamma=d/Dw$ is less than 1, a particle 121 has the diameter d of the same order of the magnitude as diameter Dw, such that $\Gamma=d/Dw$ is approximately equal 1, and particle 131 has the diameter d larger than diameter Dw, such that $\Gamma=d/Dw$ is larger than 1, as shown in FIG. 1. As shown in FIG. 1, for particle 111 having $\Gamma=d/Dw<<1$ that is approximately uniformly illuminated, the light intensity of the refracted light 113 is greater than that of the reflected light 114. For particle 131, having $\Gamma=d/Dw>>1$, and passing on certain trajectories through the Gaussian intensity beam, the light scattering efficiency for either of the refracted light 133 or the reflected light 134 is dominant, as shown in FIG. 1. For particle 121, having $\Gamma=d/Dw\sim1$, the light intensity of the refracted light 123 is the same order of the magnitude as that of the reflected light 124, as shown in FIG. 1. Particle 121 is non-uniformly illuminated because of the significant difference in the incident intensities of the laser beam at points 125 and 126 of particle 121, as shown in FIG. 1. The non-uniform illumination of particle 121 by a laser beam having a Gaussian intensity profile 122, as shown in FIG. 1, causes the intensities of the reflected and refracted components of the scattered light to be comparable in magnitude for particles passing on certain trajectories through the beams. As shown in FIG. 1, for the particles 121 having diameter d that is the same order of the magnitude as a focused Gaussian laser beam diameter Dw, the light scattered by reflection and the light scattered by refraction have similar intensities when passing on certain trajectories through the beams. The light scattered by reflection and refraction components having similar intensities forms a complex interference fringe pattern and can produce a progressively increasing magnitude of measurement error.

Thus, the Gaussian intensity profiles of the incident laser beams and the random trajectories of particles through the crossing laser beams can cause the intensities of the light scattered from the spherical objects due to different light scattering mechanisms, e.g., reflection and refraction, to be of similar order of magnitude. Additionally, because the sign of the phase shift for the interference fringe pattern produced by reflected light is opposite to that produced by refracted light, the fringes produced by reflection appears to move in the opposite direction to the fringes produced by refraction. The light scattered from the spherical object by the various mechanisms, e.g., refraction and reflection, mixes to produce the interference fringe pattern that is complex and not spatially periodic.

The simultaneous detection of more than one of the light scattering components mixed together limits the measurement resolution and leads to significant errors in determining the size and velocity of the spherical objects. The problem becomes more serious as the diameter of the spherical object approaches the diameter of the focused laser beam. In such cases, the size of the particles passing on certain trajectories through the beams may be grossly overestimated. That is, complex non-periodic interference pattern formed by the mixed light scattered from the spherical object due to various scattering mechanisms leads to significant errors in measuring the size and velocity of the spherical object that severely impacts the device performance. More than one spherical object passing the measurement volume at one time may lead to significant error in measuring the size and velocity of the spherical object. These problems are related since a larger sample volume will lead to a great probability of having more than one object in the sample volume at one time. Decreasing the size of the measurement volume to reduce the occurrence of these coincident events leads to the trajectory problem when using Gaussian beam intensity profiles.

SUMMARY

Methods and apparatuses for validating signals to determine sizes and velocities of spherical objects, e.g., particles, drops, bubbles, and the like, are described. Light is scattered from a spherical object to form an interference fringe pattern. Portions of the interference fringe pattern are received by photodetectors. The photodetectors generate time varying electrical signals in response to receiving the scattered light signal. At least one of the time varying electrical signals is partitioned into timing segments. Timing segments are processed to determine one or more timing parameters. The timing parameter consistency between at least two of the timing segments is verified. At least one of the time varying signals is validated for a periodicity based on the timing parameter consistency. The timing parameter difference between at least two of the timing segments is determined and compared to a predetermined timing parameter error threshold. The time varying electrical signal is accepted as a periodic signal for determining the size and velocity of the spherical object if the timing parameter difference is less than or equal to the timing parameter error threshold. The time varying electrical signal is rejected for determining the size and velocity of the spherical object if the timing parameter difference is larger than the timing parameter error threshold. For one embodiment, at least three photodetectors are used to produce at least three phase difference measurements providing a redundant check on the validity of the measurements of the spherical objects.

Other features and advantages of embodiments of the present invention will be apparent from the accompanying drawings and from the detailed description that follows below.

BRIEF DESCRIPTION OF THE DRAWINGS

The present invention is illustrated by way of example and not limitation in the figures of the accompanying drawings, in which like references indicate similar elements, in which:

FIG. 3 is a flowchart of one embodiment of a method to validate signals to determine sizes and velocities of spherical objects, e.g., particles, drops, bubbles, and the like;

FIG. 4 is a flowchart of another embodiment of a method to validate signals to determine sizes and velocities of spherical objects, e.g., particles, drops, bubbles, and the like;

FIG. 5 is a flowchart of another embodiment of a method to validate signals to determine sizes and velocities of spherical objects, e.g., particles, drops, bubbles, and the like;

FIG. 8 shows one embodiment of a Doppler burst signal generated by a photodetector in response to receiving the scattered light from a spherical object as it passes through crossing laser beam;

FIG. 9 is a flowchart of one embodiment of a method to determine sizes of spherical objects, e.g., particles, drops, bubbles, and the like;

FIG. 11 is a flowchart of another embodiment of a method to validate signals to determine sizes and velocities of spherical objects, e.g., particles, drops, bubbles, and the like;

FIG. 13 is a flowchart of another embodiment of a method to validate signals to determine sizes and velocities of spherical objects, e.g., particles, drops, bubbles, and the like;

DETAILED DESCRIPTION

Figure 1:
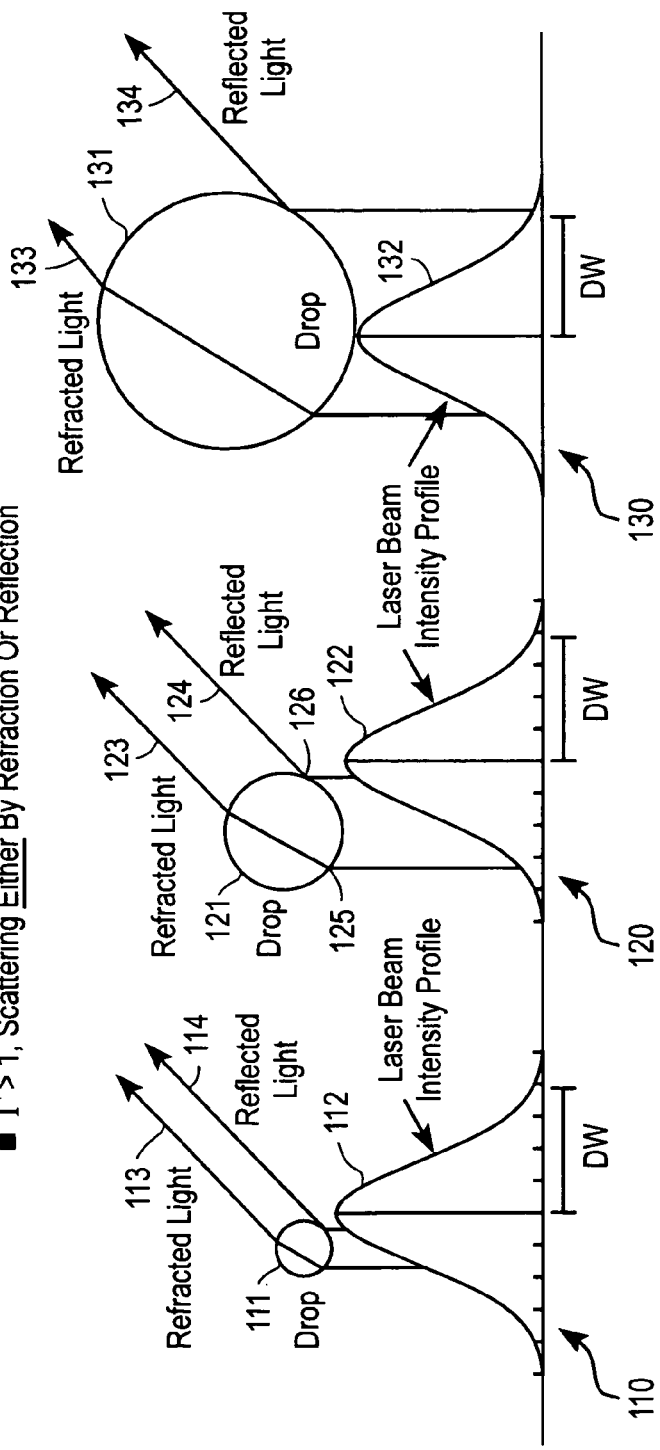
FIG. 1 illustrates drops having different diameters that pass Gaussian laser beams.

Methods and apparatuses for validating signals to determine sizes and velocities of spherical objects, e.g., particles, drops, bubbles, and the like, are described. Portions of the interference fringe pattern formed by the light scattered from a spherical object are received by photodetectors. In response, photodetectors generate time varying electrical signals. At least one of the time varying signals is partitioned into timing segments that follow each other in time. The timing segments are processed to determine one or more timing parameters, e.g., a phase and a frequency. A timing parameter consistency between at least two of the timing segments is verified. For one embodiment, the timing parameter consistency between at least one of the timing segments of the time varying signal and the time varying signal as whole is verified. At least one of the time varying signals is validated, e.g., for a periodicity, based on the timing parameter consistency. For one embodiment, to verify the consistency of the timing parameter, a timing parameter difference between at least two of the timing segments and/or the timing parameter difference between at least one of the timing segments and the time varying signal as a whole is obtained. The timing parameter difference is then compared to the timing parameter error threshold. The time varying electrical signal is accepted as a periodic signal for determining the size and velocity of the spherical object if the timing parameter difference is less or equal to a timing parameter error threshold. The time varying electrical signal is rejected for determining the size and velocity of the spherical object if the timing parameter difference is larger than the timing parameter error threshold.

Further, phase differences between each of the time varying signals from each the photodetectors are determined. The estimated sizes of the spherical object are determined based on the phase differences. Next, the time varying signals are validated based on the estimated sizes for determining the actual size and velocity of the spherical object. The time varying signals are accepted for determining the actual size and velocity of the spherical object if all estimated sizes of the spherical object are within a size error range. The time varying signals are rejected for determining the size and velocity of the spherical object if at least one estimated size of the spherical object is outside of the size error range.

Further, a signal-to-noise ratio of each of the photodetectors is determined. The time varying signals are validated for determining the size and velocity of the spherical object based on the signal-to-noise ratio of each of the photodetectors. The time varying signals are rejected for determining the size and velocity of the spherical object if the signal-to-noise ratio of at least one of the photodetectors is less or equal to a signal-to-noise ratio limit. The time varying signals are accepted for determining the size and velocity of the spherical object if the signal-to-noise ratio of all photodetectors is larger than the preset signal-to-noise ratio limit.

Further, an amplitude of each of the time varying signals is determined. The time varying signals are validated for determining the size and velocity of the spherical object based on the amplitude of each of the time varying signals.

Figure 2:
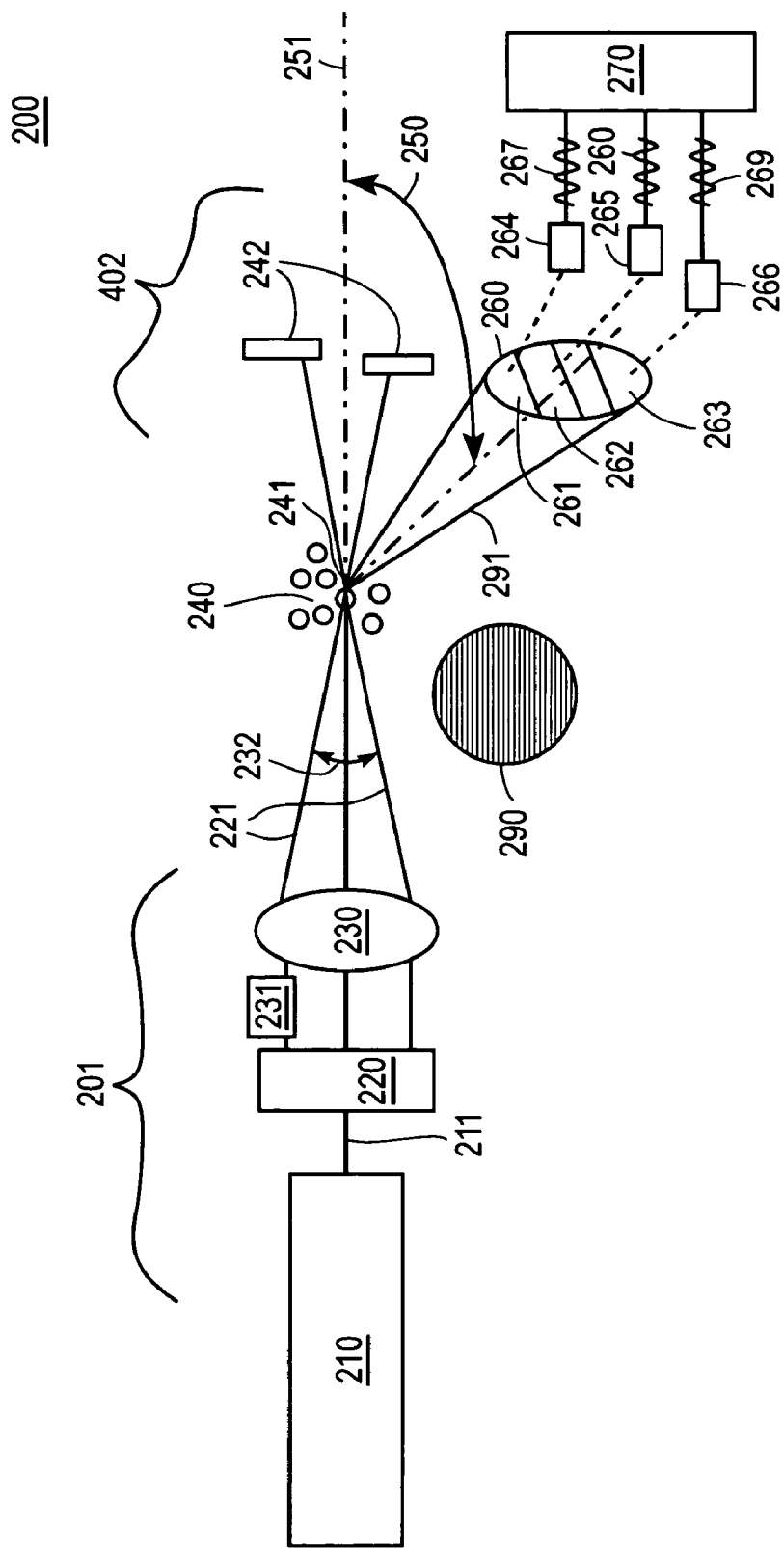
FIG. 2 shows one embodiment of an apparatus for determining the size and velocity of spherical objects.

FIG. 2 shows one embodiment of an apparatus for determining the size and velocity of spherical objects. An apparatus 200 has a transmitter 201 and a receiver 202. Transmitter 201 includes a laser 210 that generates a laser beam 211, a beam splitter 220 and a focusing optics 230. As shown in FIG. 2, laser beam 211 is split by beam splitter 220 into two beams 221 of about the same intensity. As shown in FIG. 2, focusing optics 230, e.g., one or more lenses, focuses beams 221 and causes them to cross each other at an angle 232 to form a sample volume 241 having an interference fringe pattern. An enlarged view of one embodiment of the interference fringe pattern 290 formed by crossing beams 221 is shown in FIG. 2. Sample volume 241 is an overlap region of beams 221 which cross each other at angle 232, as shown in FIG. 2. For one embodiment, angle 232 depends on the size of measured particle. For one embodiment, increasing angle 232 increases the difference between the phase of light scattered by refraction and reflection, allowing more effective discrimination between refraction and reflection components of the scattered light. For one embodiment, angle 232 formed by crossing beams 232 is in the approximate range of 1 to 20 degrees. For one embodiment, each of the laser beams 221 at the overlap region has a Gaussian or other light intensity profile. For an embodiment, beam splitter 220 and focusing optics 230 of transmitter 201 are commercially available optical components known to one of ordinary skill in the art of optical transmitter manufacturing.

As shown in FIG. 2, one of the beams 221 generated by laser 210 is modulated with a frequency by a modulator 231 to provide frequency shifting. The frequency shifting is used to compress the frequency dynamic range and resolve the direction ambiguity that would occur for spherical objects passing in a reverse direction. For one embodiment, the frequency of the modulator 231 to modulate one of the laser beams 221 is in the approximate range of 20 to 60 Megahertz ("MHz"). For an embodiment, the modulator 231 modulates one of the laser beams 221 is an acousto-optical modulator. For one embodiment, the modulator 231 to modulate one of the laser beams 221 is a Bragg cell. Bragg cells are known to one of ordinary skill of optical transmitter manufacturing.

For one embodiment, each of the Gaussian laser beams 221 is first clipped to remove light on the wings of the Gaussian curve at some desired level (e.g., $I/I_o = 1/e^2$) to reduce the size of the sample volume and decrease the number of signals to be processed that will ultimately be rejected in at signal validation operations. Clipping the wings of the Gaussian curve the laser beams also helps to better define the particle detection region needed in analyzing the results for estimating particle number density and flux.

An optical receiver collecting optics 260 is positioned at an off-axis detection angle 250 from the transmitted beam direction. For one embodiment, off-axis detection angle 250 is in the approximate range of 20-40 degrees from direction 251 of transmitting beams 221. The light from crossing beams 221 is scattered by spherical objects 240, e.g., particles, drops, bubbles, and the like, passing through sample volume 241 located at the intersection of the beams 221. The light from each of the two laser beams 221 scattered from one of the spherical objects 240 by various scattering mechanisms, e.g., refraction and reflection, interferes to form a spatially and temporally varying fringe pattern 291 on receiver optics 260. The collecting optics 260 of the receiver 202 collects the interference fringe pattern formed by the scattered light, partitions the interference fringe pattern into three portions 261, 262 and 263, and directs them on to three spaced apart photodetectors 264, 265 and 266. As shown in FIG. 2, each of the photodetectors 264-266 receives a respective portion 261-263 of the interference fringe pattern produced by the light scattered from one of the spherical objects 240. For one embodiment, the detectors 264, 265 and 266 are located in the interference fringe pattern, or an image of it, and the separation between the detectors 264, 265 and 266 is known.

When the spherical object, e.g., a particle, drop, bubble, and the like, is moving, a Doppler shift in the frequency of the scattered light occurs. The difference in the Doppler frequency shift between the light scattered from each of the beams 221 causes the fringe pattern to appear to move. As the interference fringe pattern sweeps past photodetectors 264-266 at the Doppler difference frequency, photodetectors 264-266 produce time varying signals 267-269. For one embodiment, when the light received by photodetectors 264-266 is scattered from the spherical object due to a single dominant scattering mechanism, e.g, either a refraction, or reflection, the interference fringe pattern is periodic, e.g., a sinusoidal wave signal. The periodic interference pattern that sweeps past photodetectors 264-266 at the Doppler difference frequency produces signals 267-269 that are identical in frequency, but shifted in phase. The phase shift φ is related to the spacing of the scattered fringe pattern through the following relationship:

$$\frac{\phi}{360°} = \frac{s}{\Lambda} \quad (1)$$

wherein s is the spacing between, for example, photodetector 264 and 265, φ is the phase shift between the signals 267 and 268, and Λ is the spacing between the fringes of the interference pattern at the location of the photodetectors 264-266 and is inversely proportional to the diameter of the spherical object.

For one embodiment, the spherical object's size may be in the approximate range of 0.5 micrometers ("um") to 1000 um, for example. To measure a velocity component, any one of photodetectors 264, 265, and 266 may be used. For one embodiment, a small aperture (not shown) is used in the receiver 202 to allow only light scattered by particles crossing a small region of the beam intersection to reach the photodetectors 264-266. The rest of the scattered light is blocked by light blockers 242 for safety reasons. The small aperture (not shown) is used in the receiver lens path to minimize the noise in the signal and limit the size of the measurement volume, as shown in FIG. 2.

Photodetectors 264, 265, and 266 are used to resolve the phase ambiguity, extend the measurement range and resolution, and to validate each of the time varying signals 267-269 for determining the size and velocity of the spherical object, as described in further detail below with respect to FIG. 10. As shown in FIG. 2, photodetectors 264-266 send time varying electrical signals 267-269 to a signal processor 270 to validate at least one of the time varying electrical signals 267-269 to determine the size and velocity of the spherical particle, as described in further detail below.

Figure 3:
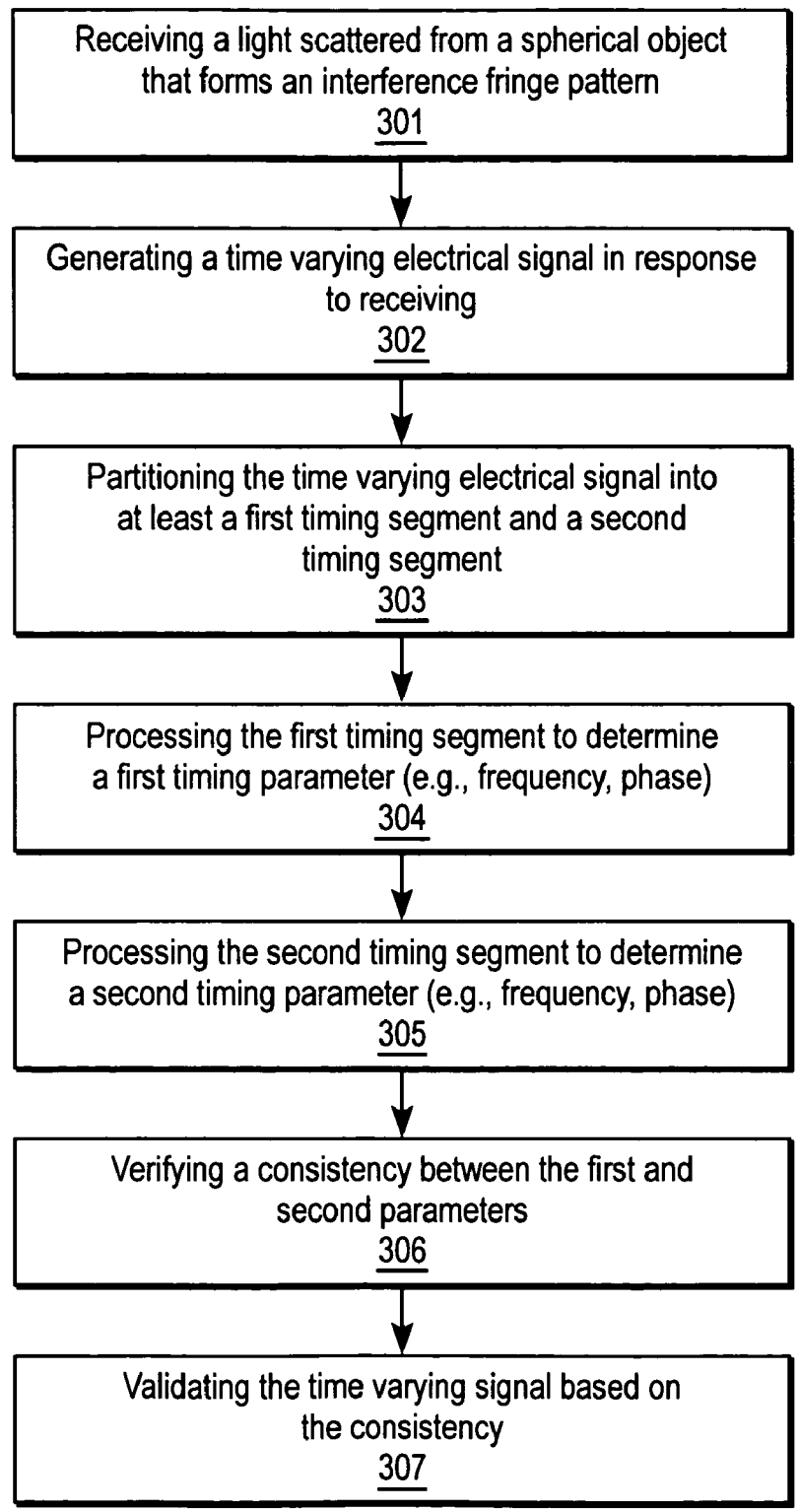

FIG. 3 is a flowchart of one embodiment of a method to validate signals to determine sizes and velocities of spherical objects, e.g., particles, drops, bubbles, and the like. Method 300 begins with operation 301 that involves receiving a light scattered from a spherical object that forms an interference fringe pattern, as described above with respect to FIG. 2. Method continues with operation 302 of generating a time varying electrical signal in response to the receiving, as described with respect to FIG. 2. Next, the operation 303 is performed that involves partitioning the time varying electrical signal into at least a first timing segment and a second timing segment.

Figure 7:
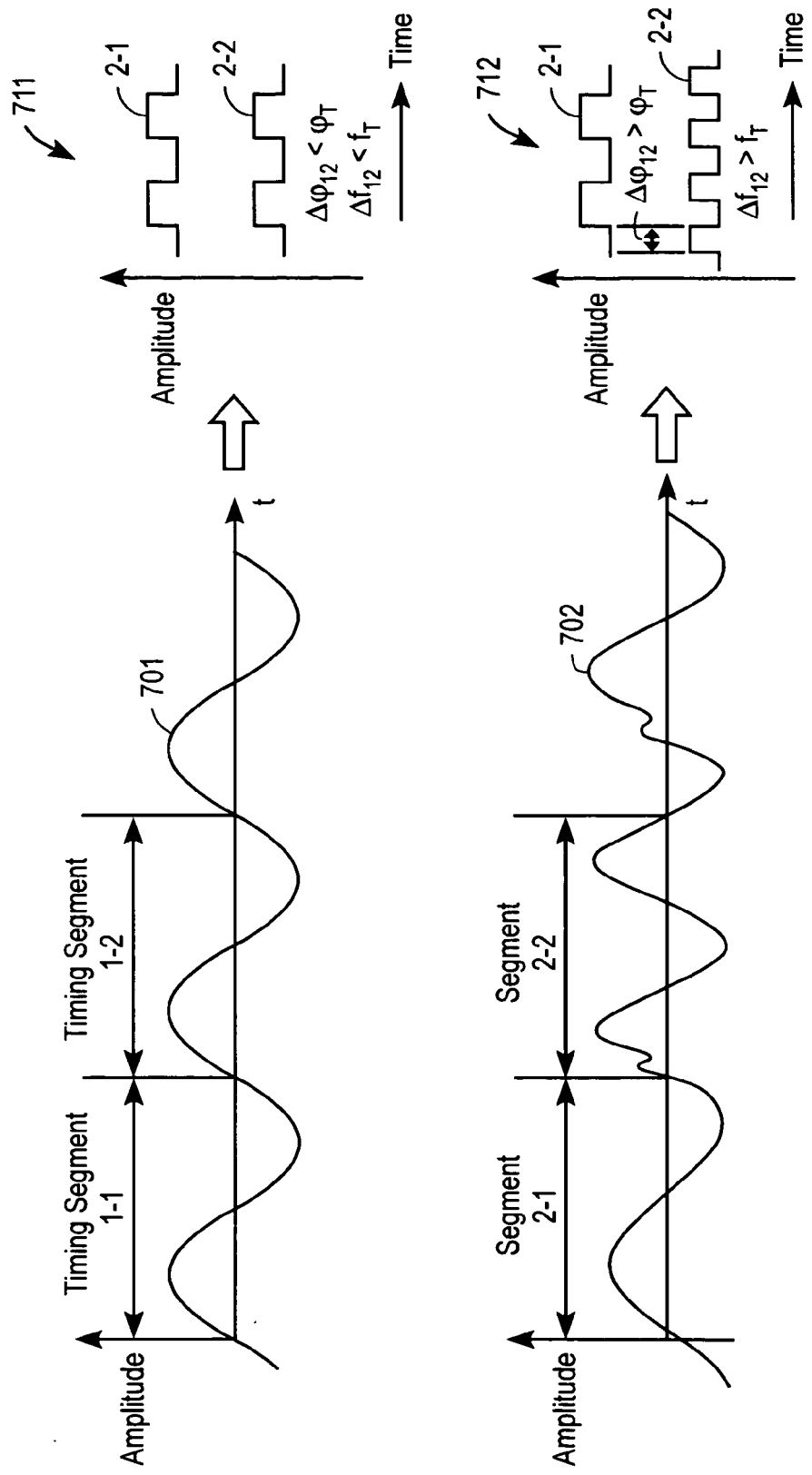
FIG. 7 shows electrical signals produced by a photodetector in response to receiving the scattered light from different spherical objects moving through the intersection of laser beams, according to one embodiment of the invention.

FIG. 7 shows electrical signals 701 and 702 produced by a photodetector in response to receiving the scattered light from different spherical objects moving through the intersection of laser beams, according to one embodiment of the invention. As shown in FIG. 7, the amplitude of each of the electrical signals 701 and 702 varies with time. Time varying electrical signal 701 is partitioned into a timing segment 1-1 and a timing segment 1-2, and time varying electrical signal 702 is partitioned a timing segment 2-1 and a timing segment 2-2, as shown in FIG. 7. Timing segment 1-2 follows timing segment 1-1 in time, and timing segment 2-2 follows timing segment 2-1 in time. For one embodiment, timing segments 1-1 and 1-2 and/or 2-1 and 2-2 have the same duration ("size"). For another embodiment, timing segments 1-1 and 1-2 and/or 2-1 and 2-2 have different sizes. For one embodiment, the number of timing segments and the duration of each of the timing segments 1-1, 1-2, and 2-1, 2-2 depend on the shape of the time varying electrical signal. For one embodiment, if one portion of the time varying signal is noisier relative to the other portions of the signal, this portion of the signal may be partitioned into more timing segments, than the other portions of the signal.

For one embodiment, partitioning includes sampling and digitizing of the time varying electrical signals 701 and 702 to obtain timing segments 1-1, 1-2, 2-1, and 2-2. Sampli and digitizing techniques are known to one of ordinary skill in the art of signal processing. For one embodiment, sampling and digitizing of the signals 701 and 702 into timing segments is performed after the signals 701 and 702 are processed using a quadrature mixing technique. The quadrature mixing technique involves mixing each of the signals 701 and 702 with a second frequency to produce a complex signal having a third frequency. The quadrature mixing technique is known to one of ordinary skill in the art of signal processing.

Referring back to FIG. 3, the operation 304 is performed that involves processing the first timing segment to determine a timing parameter of the first timing segment. Next, the operation 305 is performed that involves processing the second timing segment to determine a timing parameter of the second segment. For one embodiment, operations 304 and 305 are performed simultaneously. For one embodiment, the processing of each of the timing segments includes performing a Fourier transform of each of the timing segments after digitizing. For one embodiment, the timing segment is processed using the Fourier transform technique to yield a phase of the timing segment. For another embodiment the timing segment is processed using the Fourier transform technique to yield a frequency of the timing segment. For yet another embodiment, the timing segment is processed using the Fourier transform technique to yield both the phase and frequency of the timing segment. The Fourier transform technique is known to one of ordinary skill in the art of signal processing.

Method 300 continues with operation 306 that involves verifying a consistency between the timing parameter of the first timing segment and the timing parameter of the second timing segment. For one embodiment, the consistency of the timing parameter between the timing segments is defined such that the timing parameter remains substantially constant over the timing segments. For another embodiment, the consistency of the timing parameter between the timing segments is defined such that the timing parameter follows logic over the timing segments. For example, the timing parameter can follow a function F, for example, frequency $f=F1(t)$ and phase $\phi=F2(t)$ over the timing segments. For one embodiment, verifying the consistency between the timing parameters of the timing segments involves determining a difference between the timing parameters of the first timing segment and the second timing segment. For one embodiment, the difference between the first timing parameter and the second timing parameter is compared to a timing parameter error threshold. The timing parameter error threshold may be, for example, less or equal to 20% of the mean value of the timing parameter. Next, the operation 307 is performed that involves validating the time varying electrical signal based on the timing parameter consistency between the timing segments. That is, the entire time varying electrical signal is accepted for further processing for determining the size and velocity of the spherical object if the timing parameters of each of the timing segments are consistent between each other. The entire time varying electrical signal is rejected for further processing for determining the size and velocity of the spherical object if the timing parameters of each of the timing segments are not consistent between each other. For one embodiment, if the timing parameters of each of the timing segments are substantially constant or follow logic over the timing segments, the entire time varying signal is accepted. If the timing parameters of each of the timing segments are not substantially constant or do not follow logic over the timing segments, the entire time varying signal is rejected. For one embodiment, the entire time varying electrical signal is accepted, if the difference between the timing parameters of each of the timing segments is less or equal to the timing parameter error threshold, e.g., less or equal to 20% of the mean value of the timing parameter. The entire time varying electrical signal is rejected if the difference between the timing parameters of each of the timing segments is larger than the timing parameter error threshold, e.g., larger than 20% of the mean value of the timing parameter. For one embodiment, in addition to processing of the timing segments, the entire time varying signal as a whole is processed to determine a timing parameter. In this case, the consistency is verified between the time varying signal and at least one of the timing segments. Thus, method 300 determines whether the time varying signal produced by the photodetector remains a periodic function, e.g., a sine wave, throughout its duration or the shape of the signal changes in time and space, such that the time varying spatial wave signal becomes a non-periodic function. The non-periodic signal indicates the presence of multiple (e.g., refraction and reflection) components in the light scattered from the spherical object that leads to an erroneous measurements of the size and velocity of the spherical object.

Referring back to FIG. 7, a diagram 711 shows square waveforms of the timing segments 1-1 and 1-2 after processing that includes digitizing. The phase and frequency of each of the timing segments can be determined relative to sampling frequency and sampling starting time, or any other reference. As shown in diagram 711, digitized square waveforms of the timing segments 1-1 and 1-2 have substantially identical frequencies f and phases $\phi$. The difference between frequencies of the timing segments 1-1 and 1-2 $\Delta f_{12}$ is less or equal to frequency error threshold $f_T$. For one embodiment, the frequency error threshold is up to 20% of the mean frequency of the timing segments. The difference between phases of the timing segments 1-1 and 1-2 $\phi_{12}$ is less or equal to a phase error threshold. For one embodiment, the phase error threshold may be up to 20% of the mean phase of the timing segments. For another embodiment, the phase error threshold is up to 20 degrees. Time varying electrical signal 701 scattered from the spherical object is validated as a periodic signal and accepted for further processing to determine the size and velocity of the spherical object. As shown diagram 712, digitized square waveforms of the timing segments 2-1 and 2-2 have different frequencies f and phases $\phi$. The difference between frequencies of the timing segments 2-1 and 2-2 $\Delta f_{12}$ is larger than frequency error threshold $f_T$. For one embodiment, the frequency error threshold is up to 20% of the mean frequency of the timing segments. As shown in diagram 712, the difference between phases of the timing segments 2-1 and 2-2 $\phi_{12}$ is larger than a phase error threshold. For one embodiment, the phase error threshold may be up to 20% of the mean phase of the timing segments. For another embodiment, the phase error threshold is up to 20 degrees. Time varying electrical signal 702 scattered from another spherical object is rejected as a non-periodic corrupted signal that can not be used for determining the size and velocity of the another spherical object.

FIG. 8 shows one embodiment of a Doppler burst generated by a photodetector in response to receiving the scattered light from a spherical object as it passes through crossing laser beam. As shown in FIG. 8, Doppler burst signal 801 after passing through a high pass filter to filter out the low frequency components, becomes symmetric. As shown in FIG. 8, Doppler burst signal 801 is superimposed on a Gaussian pedestal 802. The duration of the burst signal is defined by a transit time $\tau$ of the spherical object trough the sample volume. The transit time $\tau$ depends on the diameter of the focused laser beam D, and the velocity v, or the spherical object as follows:

$$\tau = D/v \qquad (2)$$

For one embodiment, the duration of the burst signal is in the approximate range of 0.1 microseconds ("usec") to 20 milliseconds ("msec").

As shown in FIG. 8, Doppler burst signal 801 is partitioned into four timing segments T1-T4 for signal validation. For one embodiment, timing segments T1-T4 have equal duration ("size"). For one embodiment, the number of timing segments and the duration of each of the timing segments 1-1, 1-2, and 2-1, 2-2 depend on the shape of the time varying electrical signal. For one embodiment, if one portion of the burst signal 801 is noisier relative to the other portions of the signal, this portion of the signal may be partitioned into a smaller number of timing segments, than the other portions of the burst signal 801. For one embodiment, if one portion of the burst signal 801 is noisier relative to the other portions of the signal, this portion of the signal may be partitioned into a smaller number of timing segments having the longer duration, than the other portions of the burst signal 801. For one embodiment, the duration the each of the timing segments is in the approximate range of the 0.1 usec to 10 msec. If the sampled signal is too short or noisy, it may only be partitioned into 2 segments or not at all.

Each of the timing segments T1-T4 is processed to determine a timing parameter, such as a phase and a frequency, as described above with respect to FIGS. 3 and 7. For one embodiment, in addition to processing of each of the timing segments T1-T4, entire Doppler burst signal 801 is processed to determine a timing parameter of Doppler burst signal 801. Next, the consistency between the timing parameters of each of the timing segments T1-T4 is verified. For one embodiment, the consistency between the timing parameters of at least one of the timing segments T1-T4 and entire Doppler burst signal 801 is verified, as described above with respect to FIGS. 3 and 7. For one embodiment, verifying the consistency involves determining a difference between the timing parameters of each of the timing segments T1-T4. For another embodiment, verifying the consistency involves determining a difference between the timing parameters of at least one of the timing segments T1-T4 and a timing parameter of entire Doppler burst signal 801. Next, entire Doppler burst signal 801 is validated based on the consistency of the timing parameters between each of the timing segments T1-T4, as described above with respect to FIGS. 3 and 7. For one embodiment, the difference between the timing parameters of each of the timing segments T1-T4 and/or the difference between the timing parameters of at least one of the timing segments T1-T4 and entire Doppler burst signal 801 is compared to a timing parameter error threshold, as described above with respect to FIGS. 3 and 7. The entire Doppler burst signal 801 is accepted for further processing for determining the size and velocity of the spherical object if the timing parameter, such as phase and frequency, remains consistent over each of the timing segments T1-T4, as described above with respect to FIGS. 3 and 7. The entire Doppler burst signal 801 is rejected from further processing for determining the size and velocity of the spherical object, if the timing parameter, e.g., phase and frequency, is not consistent over each of the timing segments T1-T4, as described above with respect to FIGS. 3 and 7.

Figure 4:
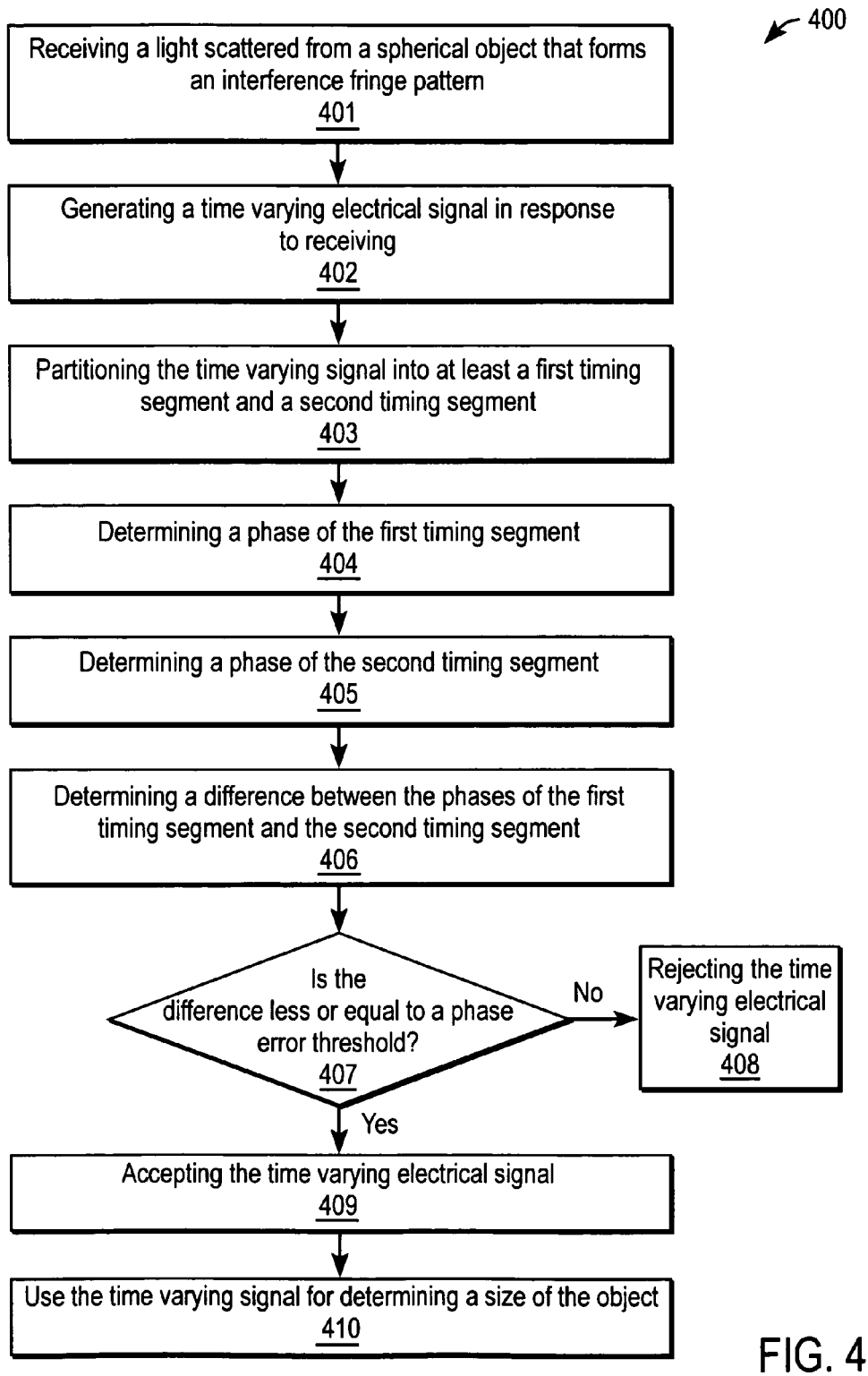

FIG. 4 is a flowchart of another embodiment of a method to validate signals to determine sizes and velocities of spherical objects, e.g., particles, drops, bubbles, and the like. Method 400 begins with operation 401 that involves receiving a light scattered from a spherical object that forms an interference fringe pattern. Method continues with operation 402 of generating a time varying electrical signal in response to the receiving, as described with respect to FIG. 2. Next, the operation 403 is performed that involves partitioning the time varying electrical signal into at least a first timing segment and a second timing segment. Next, the operation 404 is performed that involves determining a phase of the first timing segment. Further, the method 400 continues with operation 405 involving determining a phase of the second timing segment, as described above with respect to FIGS. 3 and 7. For one embodiment, operations 404 and 405 are performed simultaneously. For one embodiment, in addition to determining the phases of the timing segments, the phase of the entire time varying signal is determined. Next, at operation 406 a difference between the phases of the first timing segment and the second timing segment is determined. Next, a decision is made at operation 407 whether the difference between the phases is less or equal to a phase error threshold. If the difference between the phases of the first timing segment and the second timing segment is larger than the phase error threshold, the time varying signal is rejected at operation 408. If the difference between the phases of the first timing segment and the second timing segment is less or equal to the phase error threshold, the time varying signal is accepted at operation 409. For one embodiment, the phase error threshold is less or equal to 20% of the mean value of the phase. For one embodiment, the phase difference between the time varying signal and at least one of the timing segments is determined and compared with the phase error threshold to make a decision about accepting or rejecting the signal for determining the size and velocity of the spherical object. Next, at operation 410, the accepted time varying electrical signal is used for further processing to determining the size of the spherical object.

Figure 5:
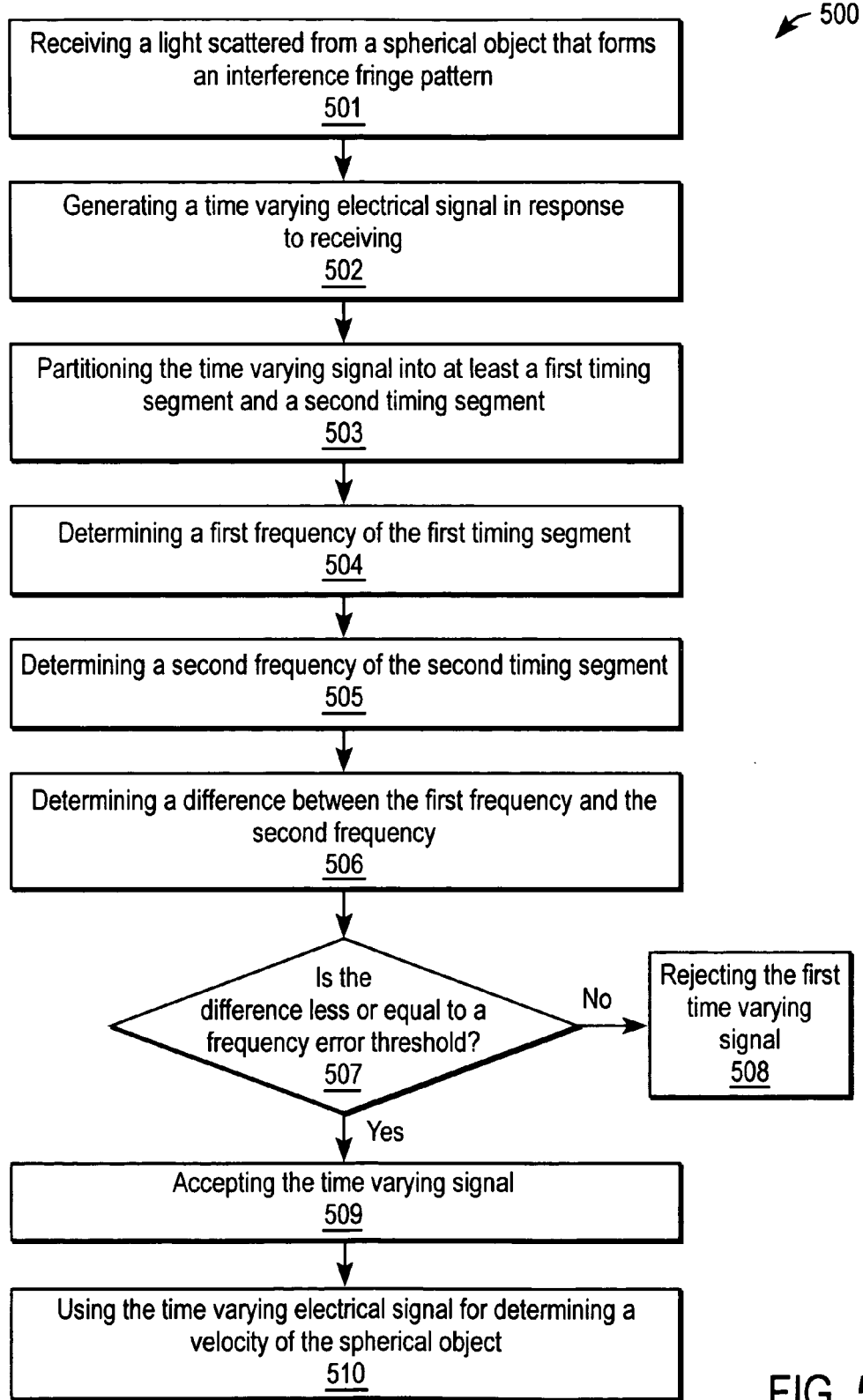

FIG. 5 is a flowchart of another embodiment of a method to validate signals to determine sizes and velocities of spherical objects, e.g., particles, drops, bubbles, and the like. Method 500 begins with operation 501 that involves receiving a light scattered from a spherical object that forms an interference fringe pattern. Method continues with operation 502 of generating a time varying electrical signal in response to receiving, as described above with respect to FIG. 2. Next, the operation 503 is performed that involves partitioning the time varying electrical signal into at least a first timing segment and a second timing segment. Next, operation 504 is performed that involves determining a frequency of the first timing segment. Further, the method 500 continues with operation 505 involving determining a frequency of the second timing segment, as described above with respect to FIGS. 3 and 7. For one embodiment, operations 504 and 505 are performed simultaneously. For one embodiment, the phase of the entire time varying signal is determined. Next, at operation 506 a difference between the frequencies of the first timing segment and the second timing segment is determined. Next, a decision is made at operation 507 whether the difference between the frequencies is less or equal to a frequency error threshold. If the difference between the frequencies of the first timing segment and the second timing segment is larger than the frequency error threshold, the time varying signal is rejected at operation 508. If the difference between the frequencies of the first timing segment and the second timing segment is less or equal to the frequency error threshold, the time varying signal is accepted at operation 509. For one embodiment, the frequency error threshold is less or equal to 20% of the mean value of the frequency of the electrical signal. Next, at operation 510, the accepted time varying electrical signal is used for further processing to determining the size of the spherical object. For one embodiment, the frequency difference between the entire time varying signal and at least one of the timing segments is determined and compared with the frequency error threshold to make a decision about accepting or rejecting the signal for determining the size and velocity of the spherical object.

Figure 9A:
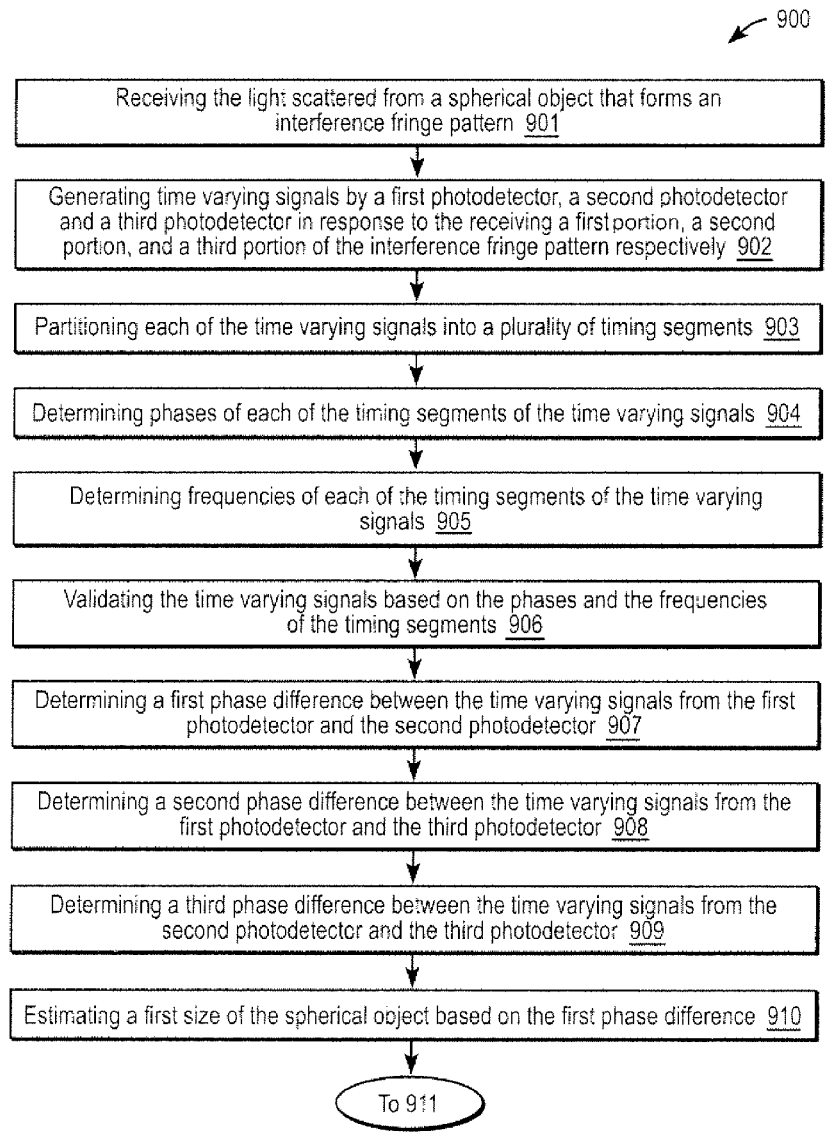
Figure 9B:
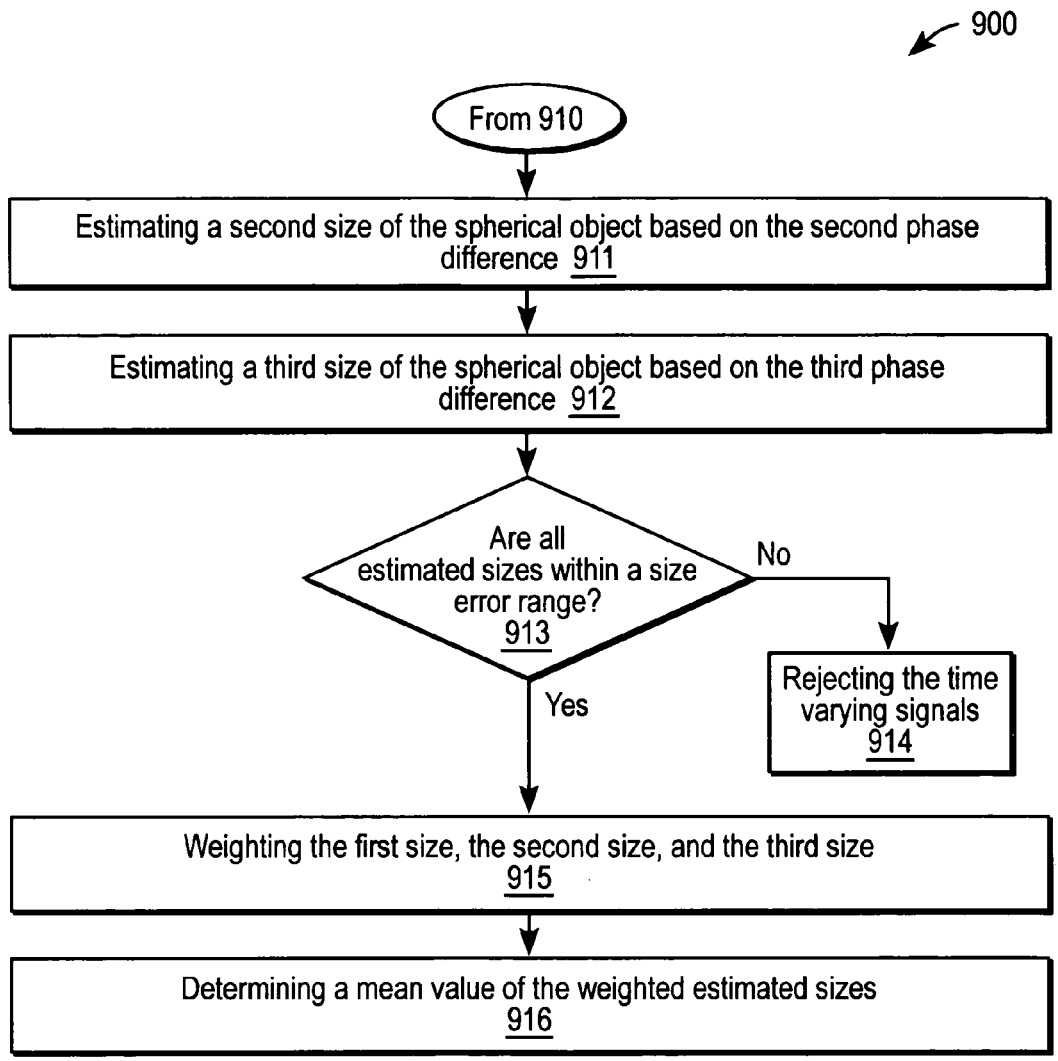

FIG. 9 is a flowchart of one embodiment of a method to determine sizes of spherical objects, e.g., particles, drops, bubbles, and the like. Method 900 begins with operation 901 that involves receiving the light scattered from a spherical object. The light scattered from the spherical object forms an interference fringe pattern. At operation 902 the scattered light is received by three photodetectors. Three photodetectors generate time varying signals in response to receiving a portion of the interference fringe pattern formed by the light scattered from the spherical object. The first photodetector receives a first portion, the second photodetector receives a second portion, and the third photodetector receives a third portion of the interference fringe pattern, as described above with respect to FIG. 2. Next, at operation 903, each of the time varying signals is partitioned into timing segments, as described above with respect to FIGS. 2-5, and 7-8. At operation 904 phases of each of the timing segments are determined, as described above with respect to FIGS. 2-5, and 7-8. At operation 905 frequencies of each of the timing segments are determined, as described above with respect to FIGS. 2-5, and 7-8. For another embodiment, operation 905 can be performed simultaneously, or before operation 904. Next, at operation 906, the time varying signals are validated based on the phases and the frequencies of the timing segments, as described above with respect to FIGS. 2-5, and 7-8. Further, method 900 continues with operation 907 of determining a first phase difference between the time varying signals from the first photodetector and the second photodetector. Next, at operation 908, a second phase difference between the time varying signals from the first photodetector and the third photodetector is determined. Further, at operation 909, a third phase difference between the time varying signals from the second photodetector and the third photodetector is determined, as described in further detail below. For one embodiment, first the phase of each of the time varying signals is determined relative to the phase of the sampling signal, as described above with respect to FIG. 3, and then the phase difference between each of the time varying signals is determined.

Figure 10:
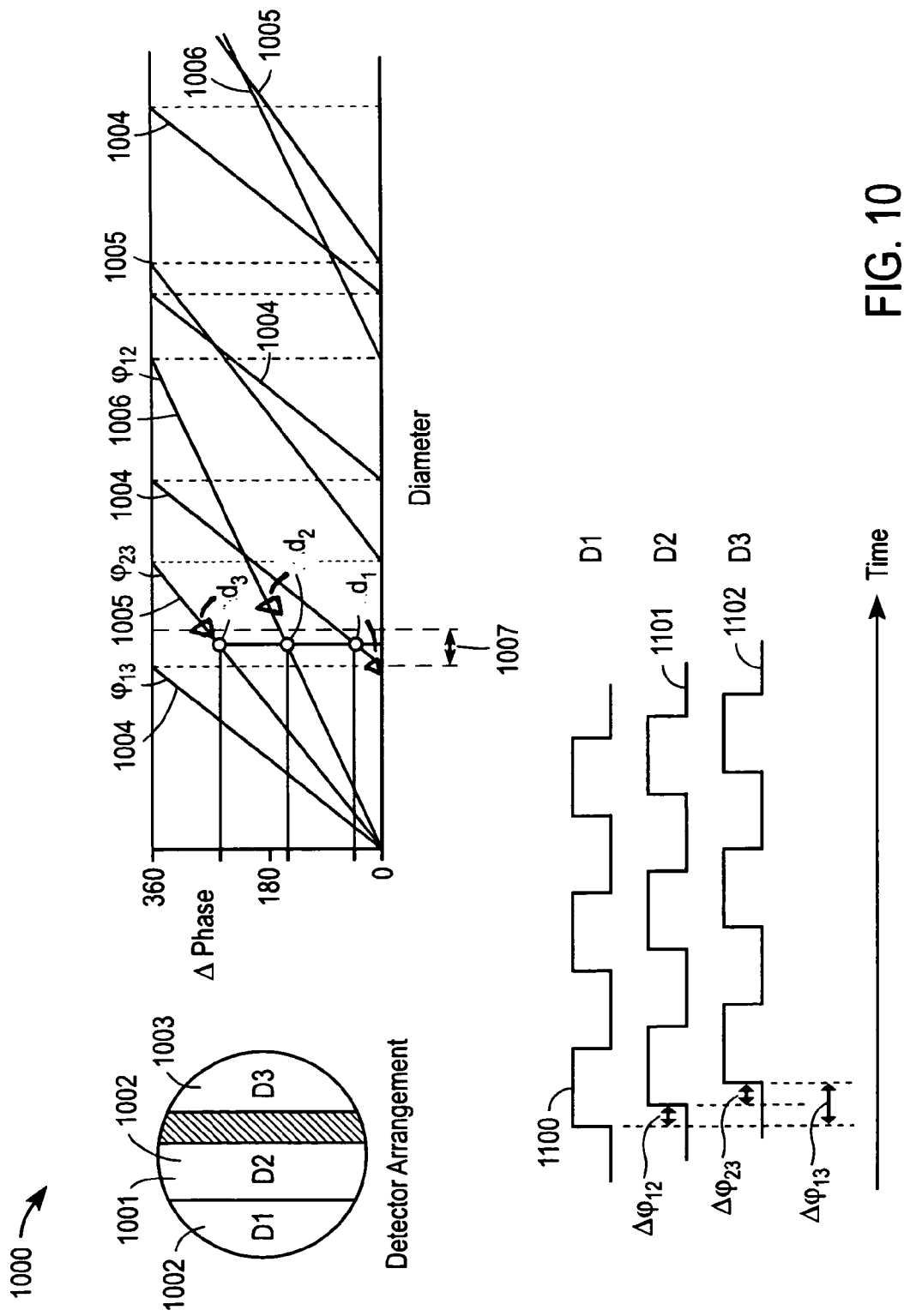
FIG. 10 illustrates a three phase measurement method to validate the signals for determining the size of the spherical objects according to one embodiment of the invention.

FIG. 10 shows a three or more phase measurement method to validate the signals for determining the size of the spherical objects according to one embodiment of the invention. As shown in FIG. 10, portions 1002, 1002, and 1003 of interference fringe pattern 1001 are received by spaced apart photodetectors D1, D2, and D3 respectively. In response to receiving portions 1002, 1002, and 1003 of interference fringe pattern 1001, the photodetectors D1, D2, and D3 generate time varying signals. FIG. 10 depicts digitized waveforms 1100, 1101, and 1102 of time varying signals from each of the photodetectors D1, D2, and D3 respectively. The phase shifts $\Delta\phi_{13}$, $\Delta\phi_{12}$, and $\Delta\phi_{23}$ between each of the photodetectors D1, D2, and D3 are measured. The phase of the time varying signal 1101 relative to the phase of the time varying signal 1100 is shifted by $\Delta\phi_{12}$, as shown in FIG. 10. The phase of the time varying signal 1102 relative to the phase of the time varying signal 1100 is shifted by $\Delta\phi_{13}$, and the phase of the time varying signal 1102 relative to the phase of the time varying signal 1102 is shifted by $\Delta\phi_{23}$. Calibration curves 1004, 1005, and 1006 show dependency of the phase shifts $\Delta\phi_{12}$, $\Delta\phi_{13}$, and $\Delta\phi_{23}$ on the diameter of a spherical object, as shown in FIG. 10. For one embodiment, calibration curves 1004, 1005, and 1006 are straight lines having different slopes. For one embodiment, curves 1004, 1005, and 1006 are computed theoretically using one of the light scattering theories, e.g., Lorenz-Mie, and geometrical optics theory. For another embodiment, calibration curves 1004, 1005, and 1006 are obtained empirically based on numerous measurements of the particles having known sizes. Slopes of the curves 1004, 1005, and 1006 indicate the sensitivity and resolution of the phase shift measurement with respect to determining the size of the spherical object, e.g., particle, droplet, bubble, and the like. The larger slope of the line indicates higher sensitivity and resolution of the measurement.

Referring back to FIG. 9, operation 910 is performed that involves estimating a first size of the spherical object based on the first phase difference. Next, operation 911 involving estimating a second size of the spherical object based on the second phase difference is performed. Next, at operation 912, a third size of the spherical object is estimated based on the third phase difference.

Referring back to FIG. 10, the estimated diameters d1, d2, and d3 of the spherical object can be determined using dependencies 1004-1006 and measured values $\Delta\phi_{13}$, $\Delta\phi_{12}$, and $\Delta\phi_{23}$. Measuring the phase difference $\Delta\phi_{23}$ between photodetectors D2 and D3 provides additional information on the spherical object and tests the sinusoidal periodicity of the interference fringe pattern. The time varying signals from each pair of photodetectors D1, D2, and D3 are validated based on the estimated sizes d1, d2, and d3. If the interference fringe pattern formed by the light scattered from the spherical object is periodic, e.g., a pure sine wave, the measured phase shifts $\Delta\phi_{13}$, $\Delta\phi_{12}$, and $\Delta\phi_{23}$ for each pair of photodetectors D1, D2, and D3 leads to substantially the same estimated particle sizes reported as d1, d2, and d3. The substantially same estimated sizes d1, d2, and d3 (first estimated sizes) are shown in FIG. 10 as circles. In this case, time varying signals from the photodetectors D1, D2, and D3 are accepted for determining size and velocity of the spherical object. If the shape of the interference fringe pattern varies in space and time, the phase shifts $\Delta\phi_{13}$, $\Delta\phi_{12}$, and $\Delta\phi_{23}$ leads to substantially different estimated sizes d1, d2, and d3, so the signals from the photodetectors D1, D2, and D3 can be discriminated and rejected. The substantially different estimated sizes d1, d2, and d3 (second estimated sizes) are shown in FIG. 10 as triangles. A validation band ("size error range") 1007 that takes into account allowable difference between measurements may be set to make a decision whether to keep or reject the signal. For one embodiment, the size error range 1007 may be set at about +/−20% of the mean value of the estimated size.

Referring back to FIG. 9, at operation 913, to validate the time varying signals, the decision is made whether all estimated sizes d1, d2, d3 are within a size error range. If at least one of the estimated sizes d1, d2, and d3 is not within the size error range, the time varying signals from the photodetectors are rejected at operation 914. If all estimated sizes d1, d2, and d3 are within the size error range, the estimated sizes are weighted in operation 915. Next, at operation 916 a mean value of the weighted estimated sizes d1, d2, and d3 is calculated to determine the size of the spherical object.

Referring back to FIG. 10, weighing coefficients a, b, and c is assigned to each of the estimated sizes d1, d2, and d3 respectively. A mean value dm of the weighted estimated sizes d1, d2, and d3 is calculated as follows:

$$dm=(a*d1+b*d2+c*d3)/3. \quad (3)$$

For one embodiment, weighing coefficients a, b, and c are chosen according to the expected sensitivity and resolution of the phase shift measurement to obtain estimated values d1, d2, and d3. For one embodiment, weighing coefficients a, b, and c are the slopes of the curves 1004, 1006, and 1005 respectively.

Figure 11A:
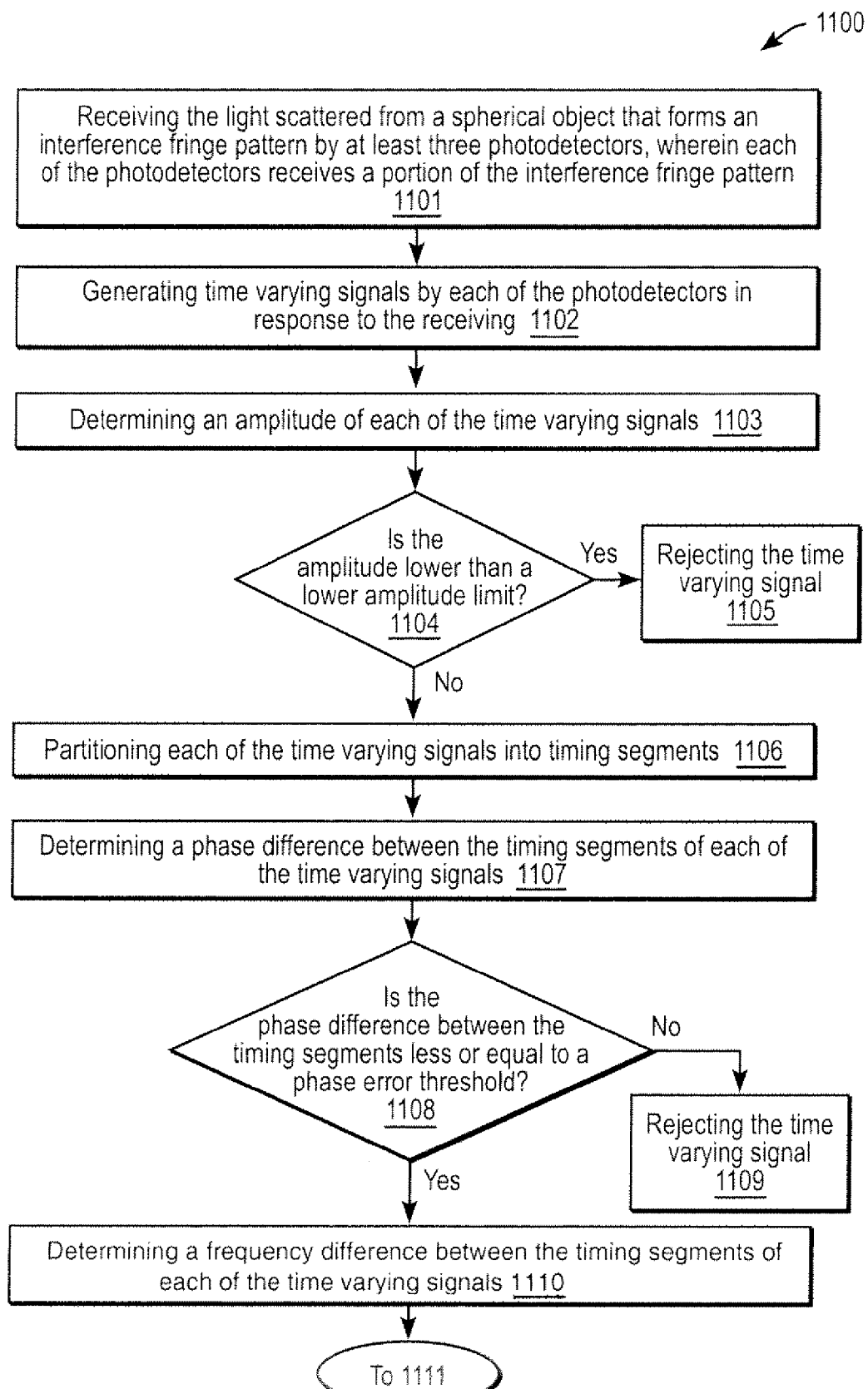
Figure 11B:
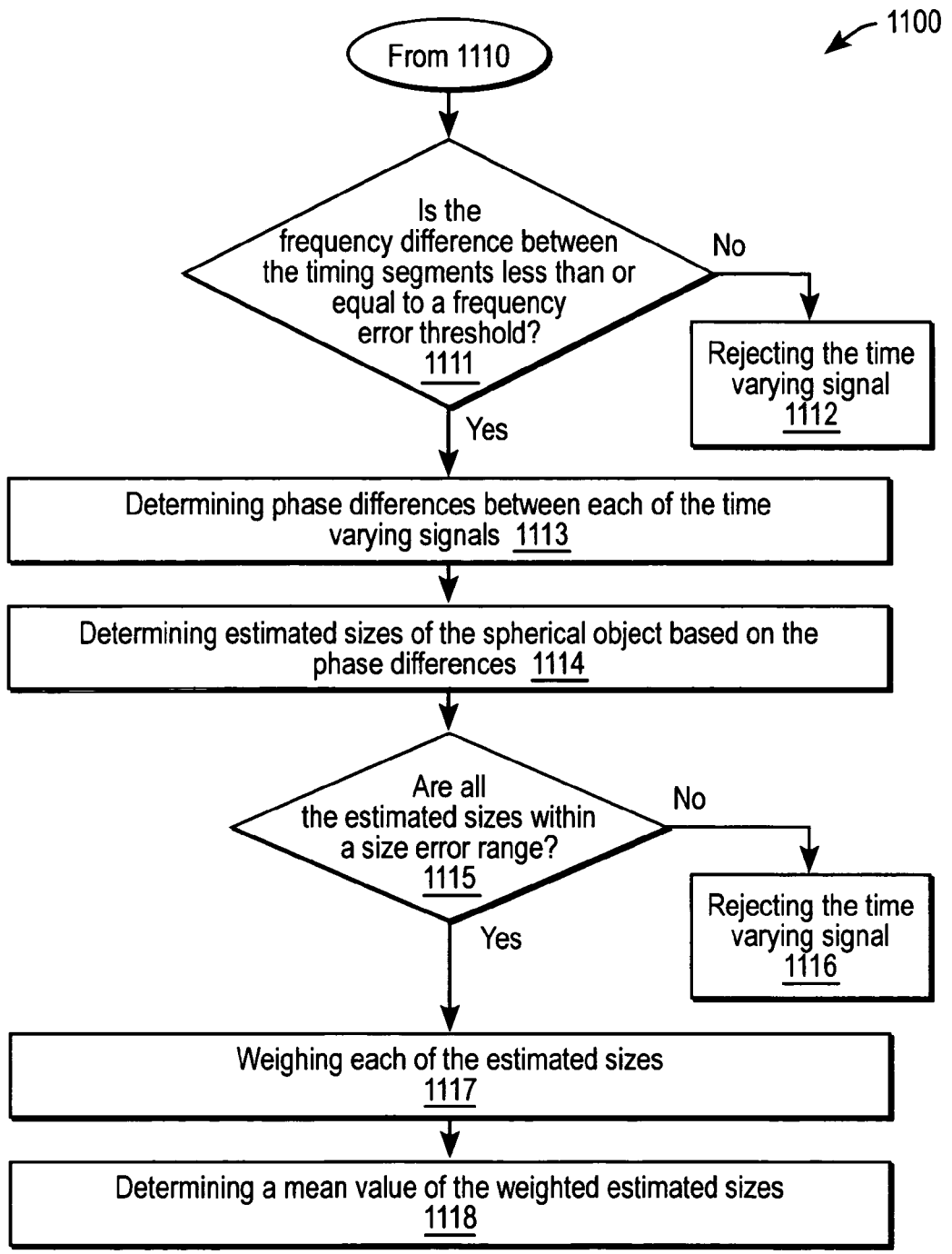

FIG. 11 is a flowchart of another embodiment of a method to validate signals to determine sizes and velocities of spherical objects, e.g., particles, drops, bubbles, and the like. Method 1100 begins with operation 1101 of receiving the light scattered from a spherical object that forms an interference fringe pattern. The light is received by at least three photodetectors. Each of the photodetectors receives a portion of the interference fringe pattern, as described above with respect to FIGS. 2, 9, and 10. Method continues with operation 1102 of generating time varying signals by each of the photodetectors in response of receiving the scattered light signal. Next, operation 1103 is performed that involves determining an amplitude of each of the time varying signals. For one embodiment, the amplitude of each of the time varying signals is measured, e.g., by a voltmeter, or any other device known to one of ordinary skill in the art of electrical measurements. The time varying signals are validated based on the amplitude to reject the signals from the spherical objects that pass the laser beams through wrong trajectories, e.g., through the edge of the laser beam, as discussed above. The light scattered from the spherical object that moves at the maximum intensity of Gaussian laser beams produces time varying signals having high amplitudes on the photodetectors. The light scattered from the spherical object that moves at the edge of the Gaussian laser beam, produces time varying signals having substantially low amplitudes on the photodetectors. The scattered light intensity I and hence, the amplitude of the signal, depends on the particle diameter d as follows:

$$I \sim d^2, \quad (4)$$

At operation 1104 a decision is made whether the amplitude is lower than a lower amplitude limit. The lower amplitude limit is set to ensure that only spherical objects that have passed at a certain point up in the Gaussian intensity laser beam are measured. At operation 1105 the time varying signal is rejected from further processing if the amplitude of the signal is lower than the lower amplitude limit. If the time varying signal is higher or equal than lower amplitude limit, the time varying signal is accepted for further processing.

Figure 12:
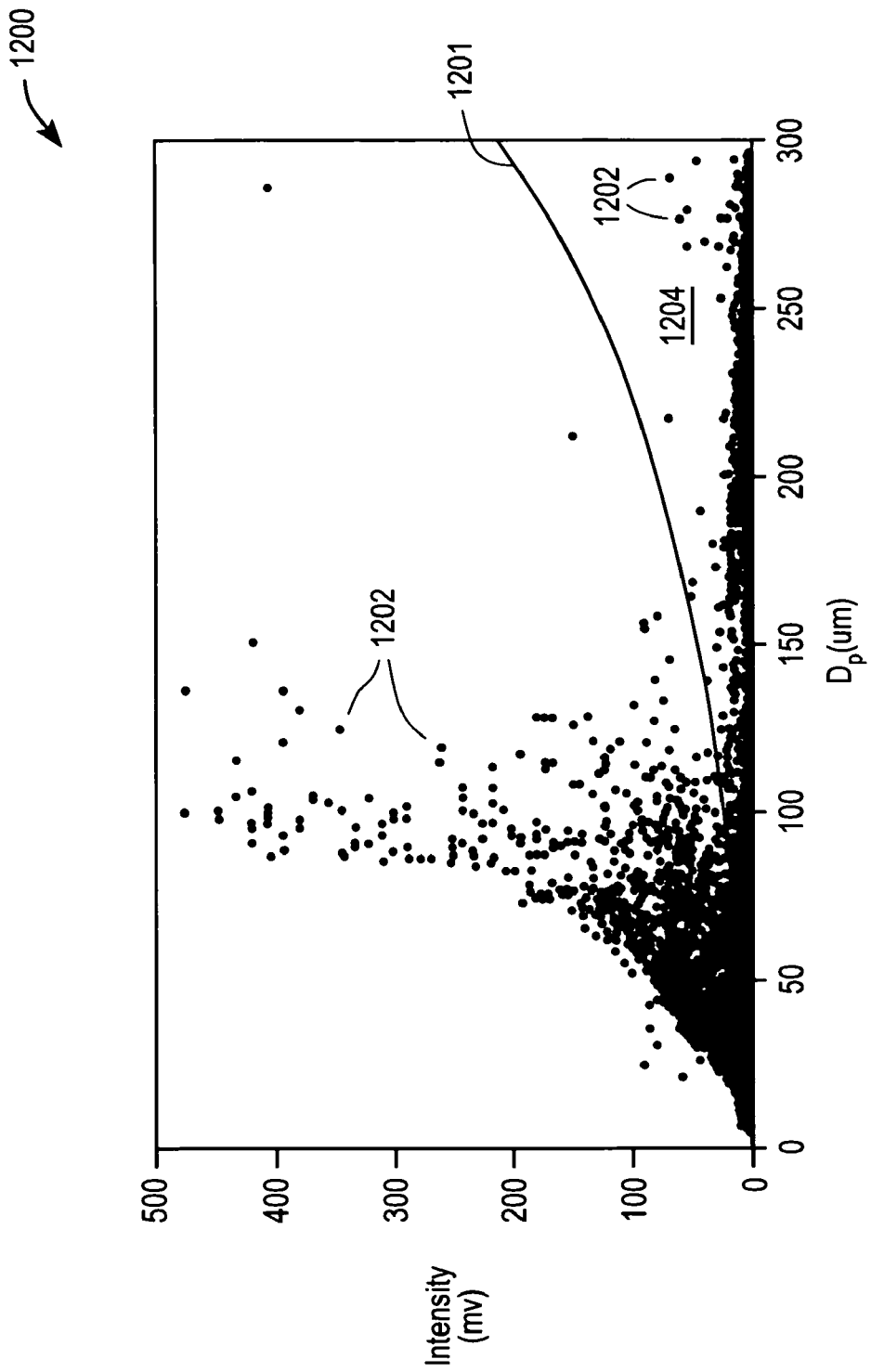
FIG. 12 is a diagram showing intensity of the electrical signal produced by the scattered light against the size of the spherical object according to one embodiment of the invention.

FIG. 12 is a diagram showing intensity of the electrical signal produced by the scattered light against the size Dp of the spherical object according to one embodiment of the invention. The sizes 1202 of the particles that have been estimated based on the measured signal intensity without using signal amplitude validation are shown in FIG. 12 as dots. For one embodiment, lower amplitude limit 1201 is set to reject the low intensity signals from the spherical objects that pass the laser beams at the edges of the Gaussian beam. As shown in FIG. 12, the sizes 1202 of the particles in area 1204 below lower amplitude limit 1201 are erroneously overestimated, as discussed above. For one embodiment, the lower amplitude limit 1201 is set at a percentage of the maximum detectable signal, so that any signals from the particles that fall below lower amplitude limit 1201 are rejected, because the particles pass on the edges of the laser beam or their size is wrongly estimated. For one embodiment, the lower amplitude limit 1201 is set in the approximate range of 0.5% to 20% of the maximum detectable signal. For one embodiment, the lower amplitude limit 1201 is the approximate range of 0.5 millivolts ("mV") to 1.5 mV and the maximum detectable signal is in the approximate range of 1 volts ("V") to 2.5 volts.

Referring back to FIG. 11, after each of the time varying signal is accepted for the further processing, at operation 1106 each of the time varying signals are partitioned into timing segments. Next, at operation 1107 the phase difference between the timing segments of each of the time varying signals is determined, as described above with respect to FIG. 4. Next, at operation 1108 the decision is made whether the phase difference between the timing segments is less or equal to a phase error threshold. For an embodiment, the phase error threshold is less or equal to 20% of the mean value of the phase. For another embodiment, the phase error threshold is up to 20 degrees. If the difference between the phases of at least one pair of the timing segments is larger than the phase error threshold, the time varying signal is rejected at operation 1109. If the difference between the phases of each of the timing segments is less or equal to the phase error threshold, at operation 1110 a frequency difference between each of the timing segments is determined, as described above with respect to FIG. 5. For alternate embodiments, operations 1107 and 1110 may be performed simultaneously, or operation 1110 may precede operation 1107. At operation 1111 the decision is made if the difference between the frequencies of at least one pair of the timing segments is less or equal to a frequency error threshold. For one embodiment, the frequency error threshold is less or equal to 20% of the mean value of the frequency. If the difference between the frequencies of at least one pair of the timing segments is larger than the frequency error threshold, the time varying signal is rejected at operation 1112. If the difference between the frequencies of each of the timing segments is less or equal to the frequency error threshold, the time varying signals are accepted to determining the phase differences between each of the time varying signals at operation 1113, as described above with respect to FIGS. 9 and 10. Next, at operation 1114, estimated sizes of the spherical object are determined based on the phase differences, as described above with respect to FIGS. 9 and 10. Next, at operation 1115 a decision is made whether all the estimated sizes are within a size error range. The time varying signals are rejected at operation 1116, if not all the estimated sizes are within the size error range. If all the estimated sizes are within the size error range, each of the estimated sizes is weighted at operation 1117. Next, at operation 1118, a mean value of weighted estimated sizes is calculated to determine the size of the spherical object, as described above with respect to FIGS. 9 and 10.

Figure 13A:
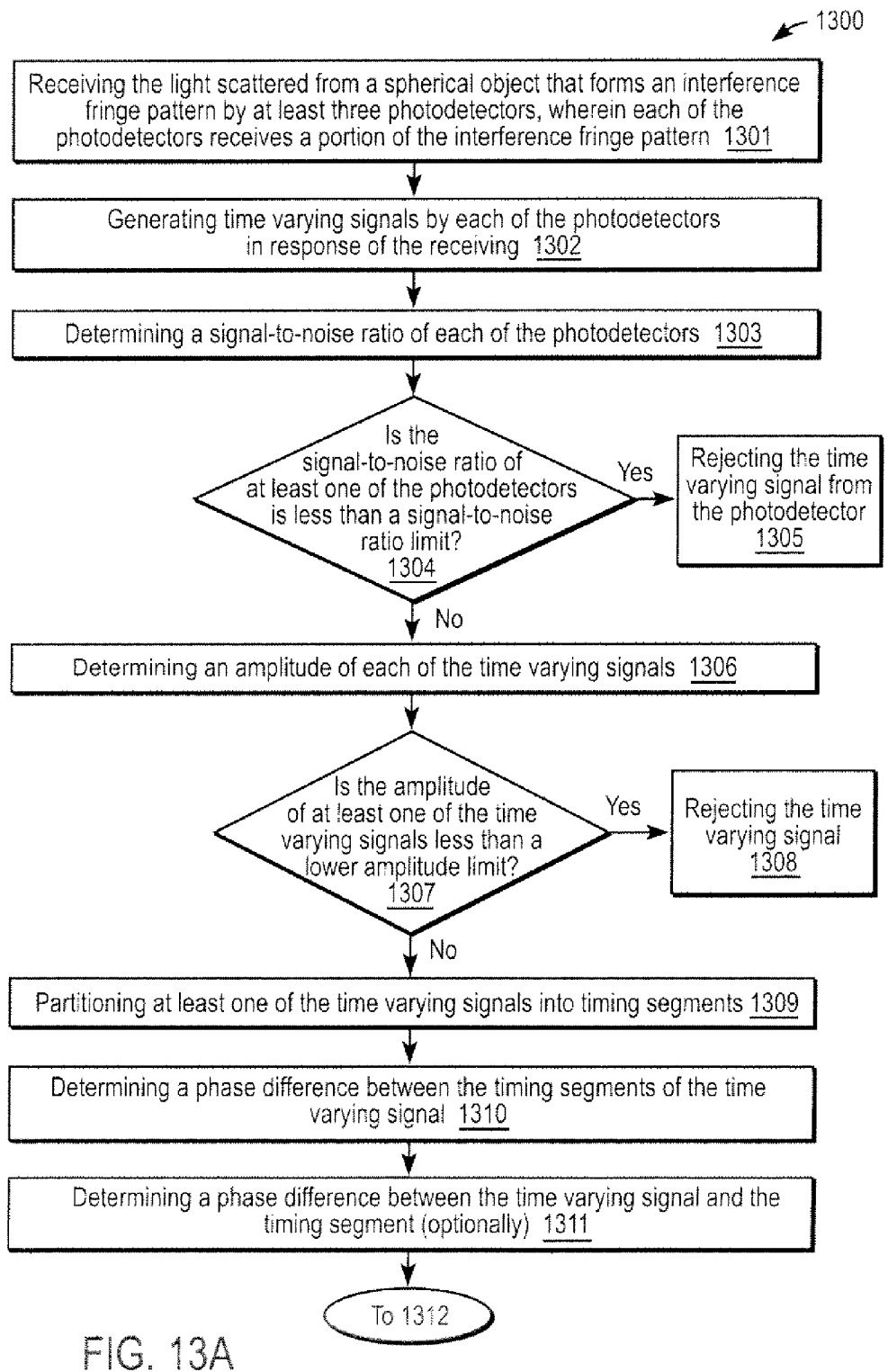
Figure 13B:
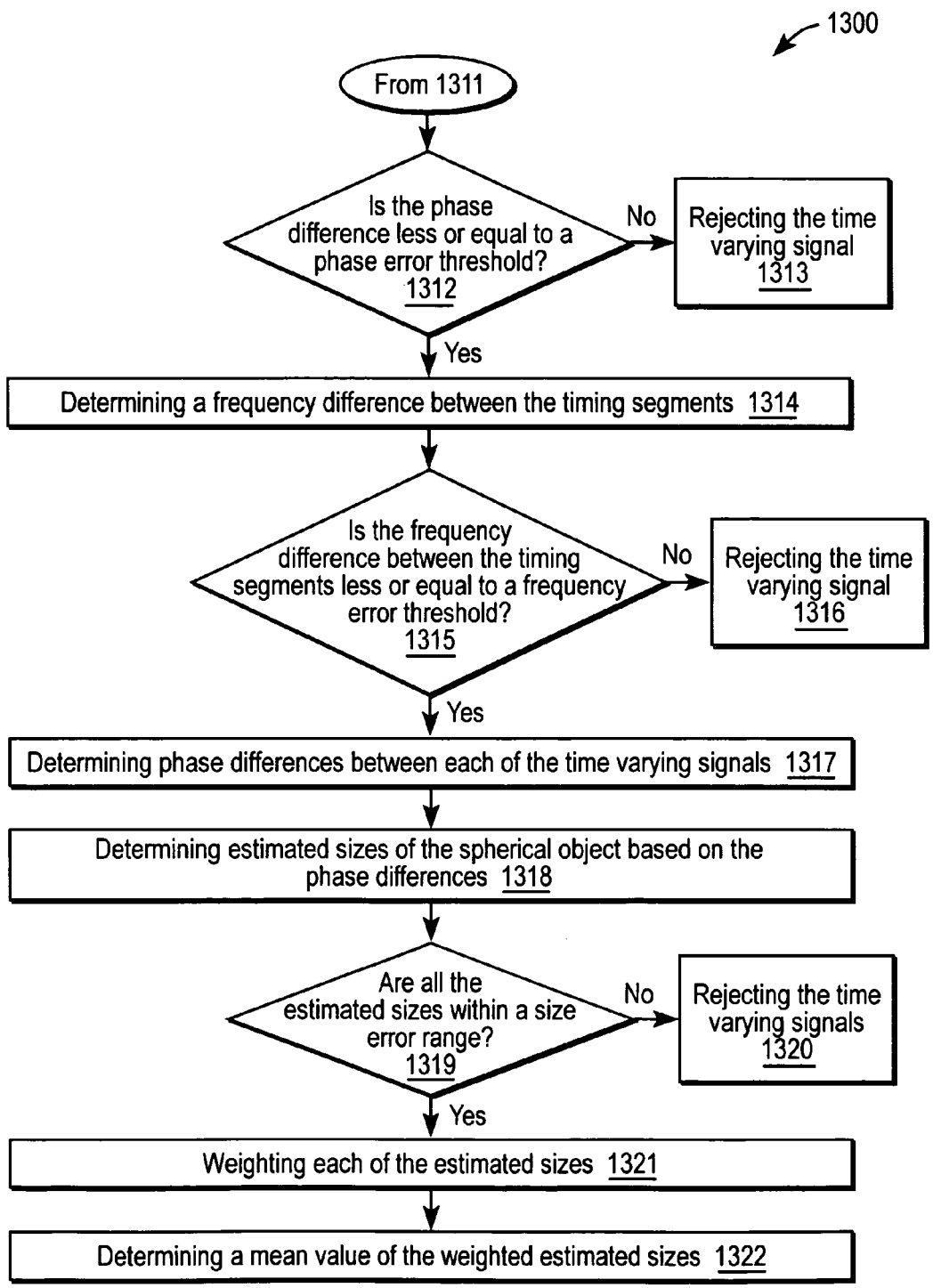

FIG. 13 is a flowchart of another embodiment of a method to validate signals to determine sizes and velocities of spherical objects, e.g., particles, drops, bubbles, and the like. Method 1300 begins with operation 1301 of receiving the light scattered from a spherical object that forms an interference fringe pattern. The light is received by at least three photodetectors. Each of the photodetectors receives a portion of the interference fringe pattern, as described above with respect to FIGS. 2, 9, and 10. Method continues with operation 1302 of generating time varying signals by each of the photodetectors in response to receiving the scattered light signal. Next, operation 1303 is performed that involves determining a signal-to-noise ratio (SNR) of each of the photodetectors to validate the time varying signals from each of the photodetectors. The time varying signals from the photodetectors are validated based on the SNR to discriminate against signals having poor SNR that may cause erroneous estimation of the size of the spherical object. For one embodiment, SNR for each of the photodetectors is computed based on the Fourier transform. Next, at operation 1304 a decision is made whether the SNR of at least one of the photodetectors is less than a SNR limit. If the SNR of at least one of the photodetectors is less than a SNR limit, the time varying signals from all photodetectors are rejected at operation 1305. If the SNR of all photodetectors is larger or equal to a SNR limit, the time varying signals from all photodetectors are accepted and used at operation 1306 to determine an amplitude of each of the time varying signals, as described above with respect to FIGS. 9 and 10. For one embodiment, validating the time varying signals from each of the photodetectors based on the SNR can be performed periodically at any stage during the execution of method 1300. For one embodiment, validating the time varying signals from each of the photodetectors based on the SNR can be performed as a part of the system initialization, during the automatic setup operation. Next, operation 1306 is performed that involves determining of an amplitude of each of the time varying signals, as described with respect to FIGS. 9 and 10. At operation 1307 a decision is made whether the amplitude is lower than a lower amplitude limit. At operation 1308 the time varying signal is rejected from further processing if the amplitude of the signal is lower than the lower amplitude limit, as described above. If the time varying signal is higher or equal than lower amplitude limit, the time varying signal is accepted for further processing. After each of the time varying signals is accepted, at operation 1309 at least one of the time varying signals is partitioned into timing segments. Next, at operation 1310 the phase difference between the timing segments of at least one of the time varying signals is determined, as described above with respect to FIG. 4. Next, operation 1311 can be optionally performed that involves determining a phase difference between the time varying signal and the timing segment, as described above with respect to FIGS. 3 and 4. Next, at operation 1312 the decision is made whether the phase difference between the timing segments is less or equal to a phase error threshold. If the phase difference is larger than the phase error threshold, the time varying signal is rejected at operation 1313. If the phase difference is less or equal to the phase error threshold, at operation 1314 a frequency difference between each of the timing segments is determined, as described above with respect to FIG. 5. For alternate embodiments, operations 1309 and 1314 may be performed simultaneously, or operation 1314 may precede operation 1314. At operation 1315 the decision is made if the difference between the frequencies of at least one pair of the timing segments is less or equal to a frequency error threshold. If the difference between the frequencies of at least one pair of the timing segments is larger than the frequency error threshold, the time varying signal is rejected at operation 1316. If the difference between the frequencies of each of the timing segments is less or equal to the frequency error threshold, the time varying signals are accepted to determining the phase differences between each of the time varying signals at operation 1317, as described above with respect to FIGS. 9 and 10. Next, at operation 1318, estimated sizes of the spherical object are determined based on the phase differences, as described above with respect to FIGS. 9 and 10. Next, at operation 1319 a decision is made whether all the estimated sizes are within a size error range. The time varying signals are rejected at operation 1320, if not all the estimated sizes are within the size error range. If all the estimated sizes are within the size error range, each of the estimated sizes is weighted according to positions of each of the photodetectors at operation 1321. Next, at operation 1322, a mean value of weighted estimated sizes is calculated to determine the size of the spherical object, as described above with respect to FIGS. 9 and 10. For one embodiment, validating the time varying signals based on the SNR, an amplitude, timing parameter consistency between the timing segments and the time varying signals, as described above, can be used to dynamically estimate a total measurement uncertainty for any condition to measure the size and velocity of the spherical object.

Figure 6:
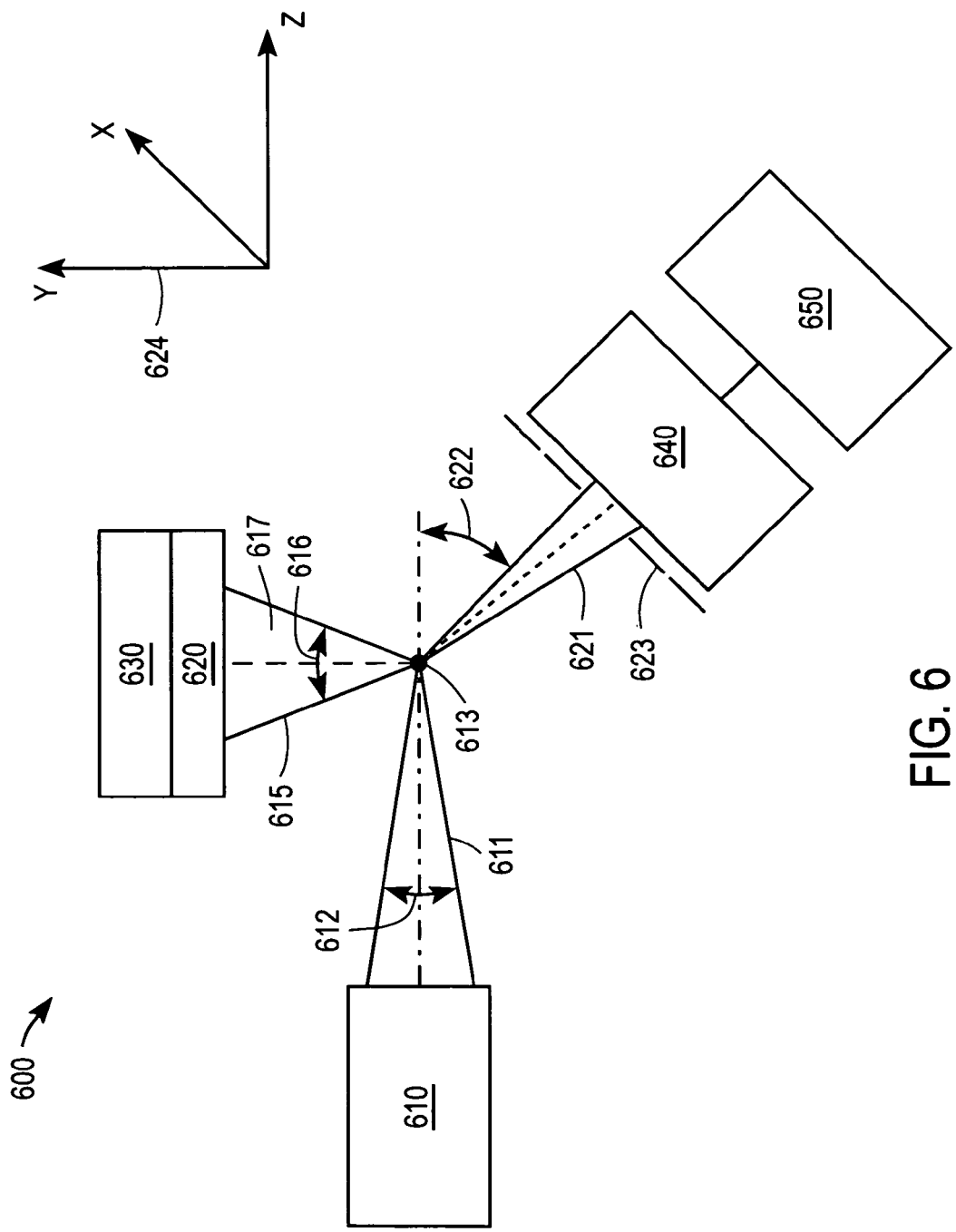
FIG. 6 shows one embodiment of an apparatus for measuring the size and three velocity components of a spherical object.

FIG. 6 shows one embodiment of an apparatus 600 for measuring the size and up to three velocity components of a spherical object. Beam propagation with respect to the Cartesian coordinate system 624 is shown in FIG. 6. The apparatus 600 has a transmitter 610 for generating a pair of coherent beams 611 propagating along an axis Z in the plane ZY and crossing each other at an angle 612 to form a sample volume 613 to measure a size and an Y-velocity component of a spherical object located inside the sample volume 613. The apparatus 600 also has a transmitter 620 that generates a pair of coherent beams 615 propagating a plane ZY along an axis Y that is perpendicular to an axis Z. The beams 615 cross each other at an angle 616 to form sample volume 613 to measure a Z-velocity component of the spherical object located inside the sample volume 613. The apparatus 600 further includes a transmitter 630 that generates a pair of coherent beams 617 propagating in a plane XY along axis Y. Beams 617 cross each other at an angle to form sample volume 613 to measure an X-velocity component of the spherical object located inside the sample volume 613. For one embodiment, the transmitter 630 is stacked on top of the 620. For one embodiment, the angles formed by each pair of coherent beams 611, 615, and 617 is in the approximate range of 1 degrees to 20 degrees.

For an embodiment, each of the transmitters 610, 620, and 630 is a compact, highly efficient, commercially available diode-pumped solid-state ("DPSS") laser having substantially high pointing stability. For one embodiment, the DPSS laser models GCL-XXX-S, BCL-XXX-S, etc., supplied by CrystaLaser of Reno, Nevada may be used. More specifically, the pointing stability of the DPSS used in transmitters 610, 620, and 630 is less than about 0.02 mrad.

For an embodiment, to simultaneously measure the size and three velocity components of the spherical object, transmitters 610, 620, and 630 generate light at a first, a second, and a third wavelength, respectively. More specifically, the first, second, and third wavelengths are, for example, violet, red, and green, respectively. For another embodiment, each of the transmitters 610, 620, and 630 generate light having a first, second, and third polarization, respectively. For yet another embodiment, two transmitters 610 and 620 generate light having a first and second wavelength respectively, with the same polarization, and the transmitter 630 generates light having the first wavelength, but the polarization is different from the polarization of the transmitters 610 and 620.

For apparatus 600 of FIG. 6, the scattered light 621 from the spherical object is collected by a receiver unit 640 to sense the scattered light 621 and convert it to time varying electrical signals. For an embodiment, the receiver unit 640 is positioned off-axis to the transmitter beams direction. The central axis of the receiver 640 forms an angle 622 relative to a propagation axis of the first pair of beams 611. For an embodiment, the angle 622 is in the approximate range of 25 to 45 degrees. For one embodiment, the angle 622 is about 30 degrees. The receiver 640 is in a plane that passes through the crossing of the beams, and is orthogonal to the plane formed by the two crossing beams. The apparatus 200 may also have a movable strip-like slit aperture 623 in front of the receiver unit 640. For one embodiment, receiver unit 640 includes photodetectors, wherein each of the photodetectors receives a portion of an interference fringe pattern formed by a light scattered from a spherical object and generates a time varying signal to produce a plurality of time varying signals, as described above. As shown in FIG. 6, signal processor 650 is coupled to receiver unit 640, wherein the signal processor is configured to partition the time varying signal into timing segments; to process the timing segments to determine one or more timing parameters of the timing segments; to verify a timing parameter consistency between at least two of the timing segments; and to validate the time varying signal based on the timing parameter consistency, SNR, and an amplitude, as described above.

Figure 14:
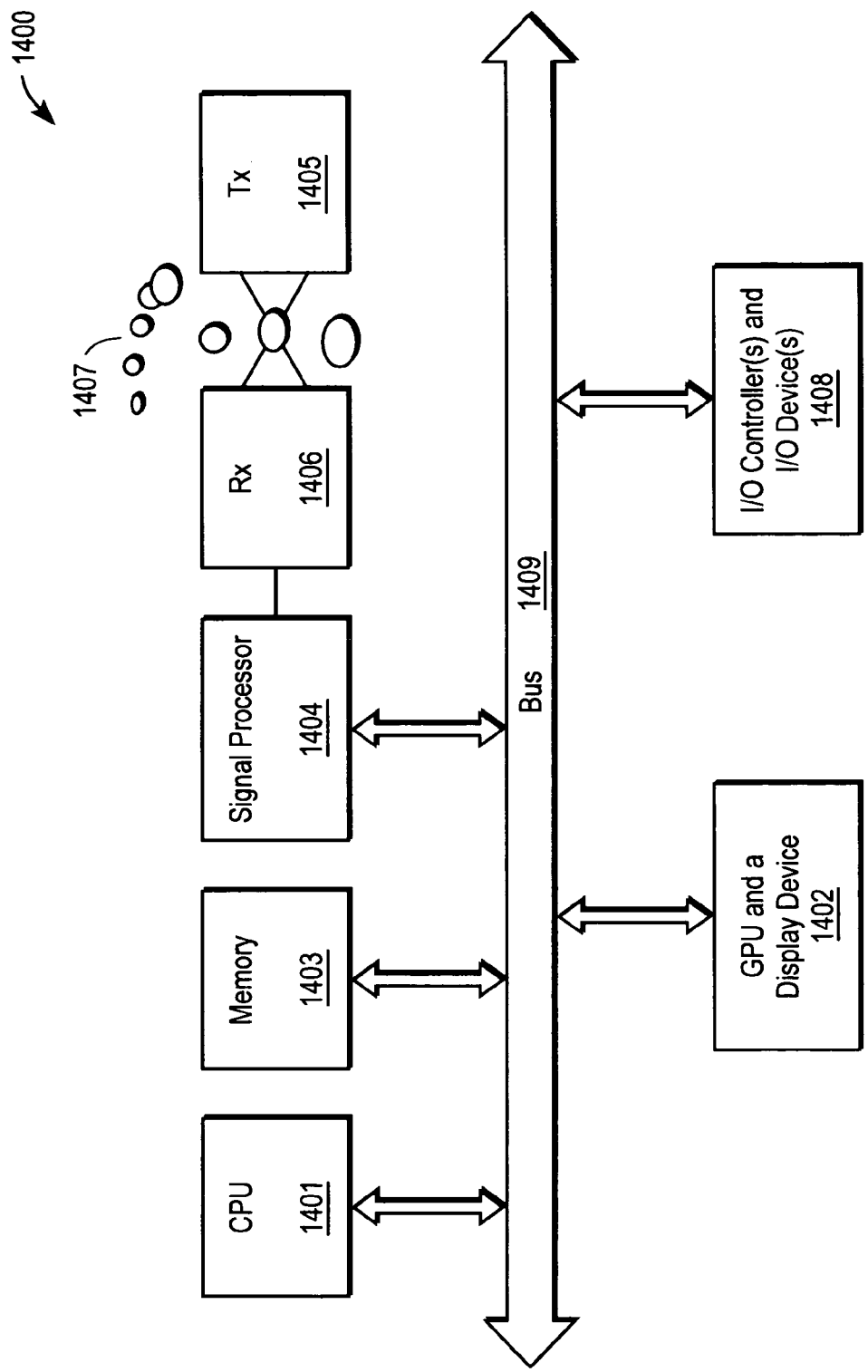
FIG. 14 illustrates one embodiment of a system to determine the size and velocity of the spherical objects.

FIG. 14 illustrates one embodiment of a system to determine the size and velocity of the spherical objects. As shown on FIG. 14, system 1400 includes a transmitter 1405 to generate coherent laser beams crossed at an angle to form a sample volume to illuminate spherical particles 1407, as described above. As shown in FIG. 14, a receiver 1406 is coupled to receive the light scattered from the spherical objects 1407, as described above. As shown in FIG. 14, receiver 1406 is coupled to signal processor 1406. As shown in FIG. 14, system 1400 includes a subsystem 1401, e.g., a CPU, a subsystem 1402, e.g., a GPU, that may be coupled with a display device, one or more subsystems 1408, e.g., one or more I/O controllers coupled to one or more I/O devices, a memory 1403 (e.g., a volatile RAM, a ROM, and a non-volatile memory, e.g., a hard drive) and a signal processor 1104, e.g., a microcontroller, coupled to a bus 1409. Signal processor 1406 is configured to perform signal validation methods as described above with respect to FIGS. 2-13. Memory 1404 may be used to store calibration curves, measured and processing data, amplitude and SNR limits, time parameter error thresholds described above.

In the foregoing specification, the invention has been described with reference to specific exemplary embodiments thereof. It will, however, be evident that various modifications and changes may be made thereto without departing from the broader spirit and scope of the invention. The specification and drawings are, accordingly, to be regarded in an illustrative rather than a restrictive sense.

The invention claimed is:

1. A method for validating signals to determine sizes and velocities of spherical objects, comprising:
   receiving a light scattered from a spherical object that forms an interference fringe pattern;
   generating a time varying electrical signal associated with the spherical object in response to the receiving;
   partitioning the time varying electrical signal associated with the spherical object into at least a first timing segment associated with the spherical object and a second timing segment associated with the spherical object;
   processing the first timing segment to determine a first timing parameter of the time varying electrical signal associated with the spherical object;
   processing the second timing segment to determine a second timing parameter of the time varying electrical signal associated with the spherical object;
   verifying a consistency between the first timing parameter of the time varying electrical signal and the second timing parameter of the time varying electrical signal; and
   validating a periodicity of the time varying electrical signal associated with the spherical object based on the consistency.

2. The method of claim 1, wherein the timing parameter is a phase.

3. The method of claim 1, wherein the timing parameter is a frequency.

4. The method of claim 1, wherein the verifying the consistency comprises
   determining a difference between the first timing parameter and the second timing parameter; and
   comparing the difference between the first timing parameter and the second timing parameter to a predetermined timing parameter error threshold.

5. The method of claim 4, wherein the validating comprises
   accepting the time varying electrical signal if the difference is less or equal to the predetermined timing parameter error threshold; and
   rejecting the time varying electrical signal if the difference is larger than the predetermined timing parameter error threshold.

6. The method of claim 1, further comprising
   determining an amplitude of the time varying electrical signal;
   validating the time varying electrical signal based on the amplitude.

7. A method for determining sizes and velocities of spherical objects, comprising:
   receiving a light from a spherical object that forms an interference fringe pattern by photodetectors, wherein each of the photodetectors receives a portion of the interference fringe pattern;
   generating time varying signals in response to the receiving;
   partitioning at least one of the time varying signals into timing segments associated with the spherical object;
   verifying a timing parameter consistency between at least two of the timing segments of the at least one of the time varying signals associated with the spherical object; and validating a periodicity of the at least one of the time varying signals based on the timing parameter consistency.

8. The method of claim 7, wherein the verifying the timing parameter consistency comprises
determining a timing parameter difference between at least two of the timing segments; and
comparing the timing parameter difference to a predetermined timing parameter error threshold.

9. The method of claim 8, wherein the validating comprises
accepting the at least one of the time varying electrical signals if the timing parameter difference is less or equal to the predetermined timing parameter error threshold; and
rejecting the at least one of the time varying electrical signals if the timing parameter difference is larger than the predetermined timing parameter error threshold.

10. The method of claim 7, further comprising
determining phase differences between each of the time varying signals from the photodetectors;
determining estimated sizes of the spherical object based on the phase differences; and
validating the time varying signals based on the estimated sizes.

11. The method of claim 10, wherein the validating the time varying signals based on the estimated sizes comprises
accepting the time varying signals if all estimated sizes of the spherical object are within a size error range; and
rejecting the time varying signals if at least one estimated size of the spherical object is outside of the size error range.

12. The method of claim 7, further comprising
determining a signal-to-noise ratio of each of the photodetectors; and
validating the time varying signals based on the signal-to-noise ratio of at least one of the photodetectors.

13. The method of claim 7, further comprising
determining an amplitude of each of the time varying signals; and
validating the time varying signals based on the amplitude of each of the time varying signals.

14. The method of claim 7, further comprising
generating at least a pair of coherent beams that cross each other at an angle to form a sample volume to illuminate the spherical object.

15. The method of claim 7, further comprising:
verifying the timing parameter consistency between at least one of the time varying signals and at least one of the timing segments.

16. An apparatus, comprising:
a receiver that includes photodetectors, wherein each of the photodetectors receives a portion of an interference fringe pattern formed by a light scattered from a spherical object and generates a time varying signal associated with the spherical object to produce a plurality of time varying signals; and
a signal processor coupled to the receiver, wherein the signal processor is configured to partition the time varying signal associated with the spherical object into timing segments associated with the spherical object; to process the timing segments to determine one or more timing parameters of the timing segments of the time varying signal associated with the spherical object; to verify a timing parameter consistency between at least two of the timing segments of the time varying signal associated with the spherical object; and to validate a periodicity of the time varying signal associated with the spherical object based on the timing parameter consistency.

17. The apparatus of claim 16, wherein the signal processor is further configured to determine a timing parameter difference between at least two of the timing segments; and
to compare the difference timing parameter between the at least two of the timing segments to a predetermined timing parameter error threshold.

18. The apparatus of claim 17, wherein the signal processor is further configured to accept the time varying signal if the timing parameter difference is less or equal to the predetermined timing parameter error threshold; and to reject the time varying electrical signal if the timing parameter difference is larger than the predetermined timing parameter error threshold.

19. The apparatus of claim 16, wherein the one or more timing parameters is a phase, a frequency, or both.

20. The apparatus of claim 16, wherein the signal processor is further configured to determine phase differences between each of the time varying signals; to determine estimated sizes of the spherical object based on the phase differences; and to validate the time varying signals based on the estimated sizes.

21. The apparatus of claim 16, wherein the signal processor is further configured to accept the time varying signals if all estimated sizes of the spherical object are within a size error range; and to reject the time varying signals if at least one estimated size of the spherical object is outside of the size error range.

22. The apparatus of claim 16, wherein the signal processor is further configured to determine a signal-to-noise ratio of each of the photodetectors; and to validate the time varying signals based on the signal-to-noise ratio of at least one of the photodetectors.

23. The apparatus of claim 16, wherein the signal processor is further configured to determine an amplitude of each of the time varying signals; and to validate the time varying signals based on the amplitude of each of the time varying signals.

24. The apparatus of claim 16, further comprising
one or more transmitters to generate at least a pair of coherent beams, wherein the pair of coherent beams cross each other at an angle to form a sample volume to illuminate the spherical object.

25. The apparatus of claim 16, wherein the signal processor is further configured to determine the timing parameter consistency between at least one of the time varying signals and at least one of the timing segments.

26. An article of manufacture, comprising:
a non-transitory machine-accessible medium including data that, when accessed by a machine, cause the machine to perform operations comprising,
receiving a light scattered from a spherical object that forms an interference fringe pattern;
generating a time varying electrical signal associated with the spherical object in response to the receiving;
partitioning the time varying electrical signal associated with the spherical object into at least a first timing segment associated with the spherical object and a second timing segment associated with the spherical object;
processing the first timing segment to determine a first timing parameter of the time varying electrical signal associated with the spherical object;
processing the second timing segment to determine a second timing parameter of the time varying electrical signal associated with the spherical object;
verifying a consistency between the first timing parameter of the time varying electrical signal associated with the spherical object and the second timing parameter of the time varying electrical signal associated with the spherical object; and validating a periodicity of the time varying electrical signal associated with the spherical object based on the consistency.

27. The article of manufacture of claim 26, wherein the timing parameter is a phase.

28. The article of manufacture of claim 26, wherein the timing parameter is a frequency.

29. The article of manufacture of claim 26, wherein the verifying the consistency comprises determining a difference between the first timing parameter and the second timing parameter; and comparing the difference between the first timing parameter and the second timing parameter to a predetermined timing parameter error threshold.

30. The article of manufacture of claim 29, wherein the validating comprises accepting the time varying electrical signal if the difference is less or equal to a predetermined timing parameter error threshold; and rejecting the time varying electrical signal if the difference is larger than the predetermined timing parameter error threshold.

31. The article of manufacture of claim 26, wherein the machine-accessible medium further includes data that cause the machine to perform operations, comprising determining an amplitude of the time varying electrical signal;

validating the time varying electrical signal based on the amplitude.

32. An article of manufacture, comprising:

a non-transitory machine-accessible medium including data that, when accessed by a machine, cause the machine to perform operations for determining sizes and velocities of spherical objects comprising, receiving a light from a spherical object that forms an interference fringe pattern by photodetectors, wherein each of the photodetectors receives a portion of the interference fringe pattern;

generating time varying signals associated with the spherical object in response to the receiving;

partitioning at least one of the time varying signals associated with the spherical object into timing segments associated with the spherical object;

verifying a timing parameter consistency between at least two of the timing segments of the at least one of the time varying signals associated with the spherical object; and validating a periodicity of the at least one of the time varying signals associated with the spherical object based on the timing parameter consistency.

33. The article of manufacture of claim 32, wherein the verifying the timing parameter consistency comprises determining a timing parameter difference between at least two of the timing segments; and comparing the timing parameter difference to a predetermined timing parameter error threshold.

34. The article of manufacture of claim 33, wherein the validating comprises accepting the at least one of the time varying electrical signals if the timing parameter difference is less or equal to the predetermined timing parameter error threshold; and rejecting the at least one of the time varying electrical signals if the timing parameter difference is larger than the predetermined timing parameter error threshold.

35. The article of manufacture of claim 32, wherein the machine-accessible medium further includes data that cause the machine to perform operations, comprising determining phase differences between each of the time varying signals from the photodetectors;

determining estimated sizes of the spherical object based on the phase differences; and validating the time varying signals based on the estimated sizes.

36. The article of manufacture of claim 34, wherein the validating the time varying signals based on the estimated sizes comprises accepting the time varying signals if all estimated sizes of the spherical object are within a size error range; and rejecting the time varying signals if at least one estimated size of the spherical object is outside of the size error range.

37. The article of manufacture of claim 32, wherein the machine-accessible medium further includes data that cause the machine to perform operations, comprising determining a signal-to-noise ratio of each of the photodetectors; and validating the time varying signals based on the signal-to-noise ratio of at least one of the photodetectors.

38. The article of manufacture of claim 32, wherein the machine-accessible medium further includes data that cause the machine to perform operations, comprising determining an amplitude of each of the time varying signals; and validating the time varying signals based on the amplitude of each of the time varying signals.

39. The article of manufacture of claim 32, wherein the machine-accessible medium further includes data that cause the machine to perform operations, comprising generating at least a pair of coherent beams that cross each other at an angle to form a sample volume to illuminate the spherical object.

40. The article of manufacture of claim 32, wherein the machine-accessible medium further includes data that cause the machine to perform operations, comprising verifying the timing parameter consistency between at least one of the time varying signals and at least one of the timing segments.

41. A system for validating signals to determine sizes and velocities of spherical objects, comprising:

means for receiving a light scattered from a spherical object that forms an interference fringe pattern;

means for generating a time varying electrical signal associated with the spherical object in response to the receiving;

means for partitioning the time varying electrical signal associated with the spherical object into at least a first timing segment associated with the spherical object and a second timing segment associated with the spherical object;

means for processing the first timing segment to determine a first timing parameter of the time varying electrical signal associated with the spherical object;

means for processing the second timing segment to determine a second timing parameter of the time varying electrical signal associated with the spherical object;

means for verifying a consistency between the first timing parameter of the time varying signal and the second timing parameter of the time varying signal; and means for validating a periodicity of the time varying electrical signal associated with the spherical object based on the consistency.

42. A system for determining sizes and velocities of spherical objects, comprising:

means for receiving a light from a spherical object that forms an interference fringe pattern by photodetectors, wherein each of the photodetectors receives a portion of the interference fringe pattern;

means for generating time varying signals associated with the spherical object in response to the receiving;

means for partitioning at least one of the time varying signals associated with the spherical object into timing segments associated with the spherical object;

means for verifying a timing parameter consistency between at least two of the timing segments of the at least one of the time varying signals associated with the spherical object; and means for validating a periodicity of at least one of the time varying signals associated with the spherical object based on the timing parameter consistency.

* * * * *